US007888323B2

(12) United States Patent
Lambris et al.

(10) Patent No.: US 7,888,323 B2
(45) Date of Patent: Feb. 15, 2011

(54) POTENT COMPSTATIN ANALOGS

(75) Inventors: John D. Lambris, Bryn Mawr, PA (US); Madan Katragadda, Ypsilanti, MI (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 371 days.

(21) Appl. No.: 11/605,182

(22) Filed: Nov. 28, 2006

(65) Prior Publication Data
US 2008/0227717 A1 Sep. 18, 2008

Related U.S. Application Data

(60) Provisional application No. 60/740,205, filed on Nov. 28, 2005.

(51) Int. Cl.
*A61K 38/10* (2006.01)
(52) U.S. Cl. .......................... 514/14; 530/327
(58) Field of Classification Search ........................ None
See application file for complete search history.

(56) References Cited

U.S. PATENT DOCUMENTS

| | | | |
|---|---|---|---|
| 4,299,838 A | 11/1981 | Durlach | |
| 4,576,750 A | 3/1986 | Pitzenberger | |
| 4,870,097 A | 9/1989 | Makovec et al. | |
| 5,167,960 A | 12/1992 | Ito et al. | |
| 5,256,642 A | 10/1993 | Fearon et al. | |
| 5,776,970 A | 7/1998 | Shechter et al. | |
| 6,169,057 B1 | 1/2001 | Lovatt | |
| 6,214,790 B1 | 4/2001 | Richelson et al. | |
| 6,319,897 B1 | 11/2001 | Lambris et al. | |
| 2001/0023066 A1 | 9/2001 | Kinder et al. | |

FOREIGN PATENT DOCUMENTS

| | | | |
|---|---|---|---|
| WO | WO 91/16345 A1 | 10/1991 | |
| WO | WO 95/23512 | 8/1995 | |
| WO | WO 99/13899 A1 | 3/1999 | |
| WO | WO 2004/026328 | * 1/2004 | |
| WO | WO 2004/026328 A1 | 4/2004 | |
| WO | WO 2004/026328 A1 | 4/2004 | |
| WO | WO 2007/044668 A1 | 4/2007 | |
| WO | WO 2007/062249 A2 | 5/2007 | |

OTHER PUBLICATIONS

Babitzke P, and Yanofsky C. (1995) Structural features of L-tryptophan required for activation of TRAP, the trp RNA-binding attenuation protein of *Bacillus subtilis. J. Biol. Chem.* 270:12452-6.
Beeley N. (1994) Peptidomimetics and small-molecule drug design: towards improved bioavailability and in vivo stability. *Trends Biotechnol.* 12:213-6.
Beene DL, Brandt GS, Zhong W, Zacharias NM, Lester HA, and Dougherty DA. (2002) Cation-pi interactions in ligand recognition by serotonergic (5-HT3A) and nicotinic acetylcholine receptors: the anomalous binding properties of nicotine. *Biochemistry.* 41:10262-9.
Dennis MS, Zhang M, Meng YG, Kadkhodayan M, Kirchhofer D, Combs D, Damico LA. (2002) Albumin binding as a general strategy for improving the pharmacokinetics of proteins. *J Biol Chem.* 277:35035-43.
Fiane AE, Mollnes TE, Videm V, Hovig T, Hogasen K, Mellbye OJ, Spruce L, Moore WT, Sahu A, and Lambris JD. (1999a) Prolongation of ex vivo-perfused pig xenograft survival by the complement inhibitor Compstatin. *Transplant. Proc.* 31:934-5.
Fiane AE, Mollnes TE, Videm V, Hovig T, Hogasen K, Mellbye OJ, Spruce L, Moore WT, Sahu A, and Lambris JD. (1999b) Compstatin, a peptide inhibitor of C3, prolongs survival of ex vivo perfused pig xenografts. *Xenotransplantation.* 6:52-65.
Fiane AE, Videm V, Lambris JD, Geiran OR, Svennevig JL, and Mollnes TE. (2000) Modulation of fluid-phase complement activation inhibits hyperacute rejection in a porcine-to-human xenograft model. *Transplant. Proc.* 32:899-900.
Furlong ST, Dutta AS, Coath MM, Gormley JJ, Hubbs SJ, Lloyd D, Mauger RC, Strimpler AM, Sylvester MA, Scott CW, and Edwards PD. (2000) C3 activation is inhibited by analogs of compstatin but not by serine protease inhibitors or peptidyl alpha-ketoheterocycles. *Immunopharmacology.* 48:199-212.
Hruby VJ. (1993) Conformational and topographical considerations in the design of biologically active peptides. *Biopolymers.* 33:1073-82.
Kalli KR, Hsu P, Fearon and DT. (1994) Therapeutic uses of recombinant complement protein inhibitors. *Springer Semin. Immunopathol.* 15:417-31.
Katragadda M, Morikis D, and Lambris JD. (2004) Thermodynamic studies on the interaction of the third complement component and its inhibitor, compstatin. *J. Biol. Chem.* 279:54987-95.
Klepeis JL, Floudas CA, Morikis D, Tsokos CG, Argyropoulos E, Spruce L, and Lambris JD. (2003) Integrated computational and experimental approach for lead optimization and design of compstatin variants with improved activity. *J. Am. Chem. Soc.* 125:8422-3.
Kozlowski A, Charles SA, and Harris JM. (2001) Development of pegylated interferons for the treatment of chronic hepatitis C. *BioDrugs.* 15:419-29.
Mallik B, Katragadda M, Spruce LA, Carafides C, Tsokos CG, Morikis D, and Lambris JD (2005) Design and NMR Characterization of Active Analogs of Compstatin Containing Non-Natural Amino Acids. *J. Med. Chem.* 48:274-286.
Morikis D, Assa-Munt N, Sahu A, and Lambris JD. (1998) Solution structure of Compstatin, a potent complement inhibitor. *Protein Sci.* 7:619-27.
Nguyen A, Reyes AE 2nd, Zhang M, McDonald P, Wong WL, Damico LA, Dennis MS. (2006) The pharmacokinetics of an albumin-binding Fab (AB.Fab) can be modulated as a function of affinity for albumin. *Protein Eng Des Sel.* 19:291-7.

(Continued)

*Primary Examiner*—Christopher R. Tate
*Assistant Examiner*—Roy Teller
(74) *Attorney, Agent, or Firm*—Potter Anderson & Corroon LLP

(57) ABSTRACT

Compounds comprising peptides and peptidomimetics capable of binding C3 protein and inhibiting complement activation are disclosed. These compounds display greatly improved complement activation-inhibitory activity as compared with currently available compounds.

25 Claims, 9 Drawing Sheets

OTHER PUBLICATIONS

Nilsson B, Larsson R, Hong J, Elgue G, Ekdahl KN, Sahu A, and Lambris JD. (1998) Compstatin inhibits complement and cellular activation in whole blood in two models of extracorporeal circulation. *Blood*. 92:1661-7.

Sahu A, Kay BK, and Lambris JD. (1996) Inhibition of human complement by a C3-binding peptide isolated from a phage-displayed random peptide library. *J. Immunol*. 157:884-91.

Soulika AM, Khan MM, Hattori T, Bowen FW, Richardson BA, Hack CE, Sahu A, Edmunds LH Jr, and Lambris JD. (2000) Inhibition of heparin/protamine complex-induced complement activation by Compstatin in baboons. *Clin. Immunol*. 96:212-21.

Spruce L., E. Argyropoulos, D. Mastellos, G. Sfyroera, and J.D. Lambris (2002) Chemical synthesis of small complement proteins and protein modules. *International Immunopharmacology*. 2: 1320-1321.

Veronese FM. (2001) Peptide and protein PEGylation: a review of problems and solutions. *Biomaterials* 22:405-417.

Wang Y, Hu Q, Madri JA, Rollins SA, Chodera A, and Matis LA. (1996) Amelioration of lupus-like autoimmune disease in NZB/WF1 mice after treatment with a blocking monoclonal antibody specific for complement component C5. *Proc. Natl. Acad. Sci. USA*. 93:8563-8.

Zhao B, Helms LR, DesJarlais RL, Abdel-Meguid SS, and Wetzel R. (1995) A paradigm for drug discovery using a conformation from the crystal structure of a presentation scaffold. *Nat. Struct. Biol*. 2:1131-7.

Bowie, et al., "Deciphering the message in protein sequences: tolerance to amino acid substitutions", Science, vol. 247, pp. 1306-1310 (1990).

Katragadda, M., et al., "Hydrophobic effect and hydrogen bonds account for the improved activity of . . . compstatin", J. Med. Chem., vol. 49, pp. 4616-4622 (2006).

Katragadda, M., et al., "Structure-activity-based design of potent compstatin analogs", Mol. Immunol., vol. 44, p. 192 (2007)[Abstract].

Klepeis, et al., "Predicting peptide structures using NMR data and deterministic global optimization", J. Comput. Chem . . . , vol. 20, pp. 1354-1370 (1999).

Morikis, et al., "Design, structure, function, . . . of compstatin", in Bioactive Peptides in Drug Discovery . . . , Matsoukas and Mavromoustakos (Eds) IOS press, pp. 235-246 (1999).

Morikis, et al., "The structural basis of compstatin activity examined by structure-function-based design . . . ", J. Biol. Chem., vol. 277, pp. 14942-14953 (2002).

Morikis, et al., "Structural aspects and design of low-molecular-mass complement inhibitors", Biochem. Soc. Transact., vol. 30, pp. 1026-1036 (2002).

Ngo, et al., Computational complexity, protein structure prediction . . . , The Prot. Folding Problem and Tert. Struct. Pred., Merz and LeGrand, eds. (1994).

Sahu, et al., "Binding kinetics, structure-activity relationship, and biotransformation of the complement inhibitor compstatin", *J. Immunol*., vol. 165, pp. 2491-2499 (2000).

Sahu, et al., "Compstatin, a peptide inhibitor of complement, exhibits species-specific binding to complement component C3", Mol. Immunol., vol. 39, pp. 557-566 (2002).

Schasteen, et al., "Synthetic peptide inhibitors of complement serine proteases—III. Significant increase in inhibitor potency . . . ", Mol. Immunol., vol. 28, pp. 17-26 (1991).

Soulika, et al., "Studies of structure-activity relations of complement inhibitor compstatin", J. Immunol., vol. 170, pp. 1881-1890 (2003).

Zacharias, et al., "Cation-Pi interactions in ligand recognition and catalysis", Trends. Pharmacol. Sci., vol. 23, pp. 281-287 (2002).

International Search Report and Written Opinion in PCT/US2006/045539, mailed Jul. 24, 2007.

Non-Final Office Action in U.S. Appl. No. 10/528,496, mailed Jun. 22, 2010.

* cited by examiner

SEQUENCE LISTING

```
<160> NUMBER OF SEQ ID NOS: 39

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: AMIDATION

<400> SEQUENCE: 1

Ile Cys Val Val Gln Asp Trp Gly His His Arg Cys Thr
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: amidation

<400> SEQUENCE: 2

Ile Cys Val Val Gln Asp Trp Gly His His Arg Cys Thr
1               5                   10

<210> SEQ ID NO 3
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: amidation

<400> SEQUENCE: 3

Ile Cys Val Tyr Gln Asp Trp Gly Ala His Arg Cys Thr
1               5                   10

<210> SEQ ID NO 4
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION,
<220> FEATURE:
<221> NAME/KEY: DISULFID
<222> LOCATION: (2)..(12)

<400> SEQUENCE: 4

Ile Cys Val Trp Gln Asp Trp Gly Ala His Arg Cys Thr
1               5                   10

<210> SEQ ID NO 5
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: amidation

<400> SEQUENCE: 5
```

```
Ile Cys Val Trp Gln Asp Trp Gly Ala His Arg Cys Thr
1               5                   10
```

<210> SEQ ID NO 6
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: D-threonine

<400> SEQUENCE: 6

```
Ile Cys Val Trp Gln Asp Trp Gly Ala His Arg Cys Thr
1               5                   10
```

<210> SEQ ID NO 7
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: X is a tryptophan analog 2-naphthalene
<220> FEATURE:
<221> NAME/KEY: MOD_RES
<222> LOCATION: (13)..(13)
<223> OTHER INFORMATION: amidation

<400> SEQUENCE: 7

```
Ile Cys Val Xaa Gln Asp Trp Gly Ala His Arg Cys Thr
1               5                   10
```

<210> SEQ ID NO 8
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: X is a tryptophan analog 2-naphthalene

<400> SEQUENCE: 8

```
Ile Cys Val Xaa Gln Asp Trp Gly Ala His Arg Cys Thr
1               5                   10
```

```
<210> SEQ ID NO 9
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: X is a tryptophan analog 1-naphthalene

<400> SEQUENCE: 9

Ile Cys Val Xaa Gln Asp Trp Gly Ala His Arg Cys Thr
1               5                   10

<210> SEQ ID NO 10
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: X is 2 indanylglycine carboxylic acid
<220> FEATURE:
<221> NAME/KEY: MOD_RES
<222> LOCATION: (13)..(13)
<223> OTHER INFORMATION: amidation

<400> SEQUENCE: 10

Ile Cys Val Xaa Gln Asp Trp Gly Ala His Arg Cys Thr
1               5                   10

<210> SEQ ID NO 11
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: X is 2 indanylglycine carboxylic acid

<400> SEQUENCE: 11

Ile Cys Val Xaa Gln Asp Trp Gly Ala His Arg Cys Thr
1               5                   10

<210> SEQ ID NO 12
<211> LENGTH: 13
```

```
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: X is dihydrotryptophan

<400> SEQUENCE: 12

Ile Cys Val Xaa Gln Asp Trp Gly Ala His Arg Cys Thr
1               5                   10

<210> SEQ ID NO 13
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: X is benzoylphenylalanine

<400> SEQUENCE: 13

Ile Cys Val Xaa Gln Asp Trp Gly Ala His Arg Cys Thr
1               5                   10

<210> SEQ ID NO 14
<211> LENGTH: 16
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)

<400> SEQUENCE: 14

Gly Ile Cys Val Trp Gln Asp Trp Gly Ala His Arg Cys Thr Ala Asn
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: Synthetic sequence
<220> FEATURE:
<221> NAME/KEY: DISULFID
<222> LOCATION: (3)..(13)

<400> SEQUENCE: 15

Gly Ile Cys Val Trp Gln Asp Trp Gly Ala His Arg Cys Thr Asn
1               5                   10                  15

<210> SEQ ID NO 16
```

```
<211> LENGTH: 15
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: 5-fluoro-l-tryptophan
<220> FEATURE:
<221> NAME/KEY: MOD_RES
<222> LOCATION: (8)..(8)
<223> OTHER INFORMATION: 5-fluoro-l-tryptophan

<400> SEQUENCE: 16

Gly Ile Cys Val Trp Gln Asp Trp Gly Ala His Arg Cys Thr Asn
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: 6-fluoro-l-tryptophan
<220> FEATURE:
<221> NAME/KEY: MOD_RES
<222> LOCATION: (8)..(8)
<223> OTHER INFORMATION: 6-fluoro-l-tryptophan

<400> SEQUENCE: 17

Gly Ile Cys Val Trp Gln Asp Trp Gly Ala His Arg Cys Thr Asn
1               5                   10                  15

<210> SEQ ID NO 18
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 5-fluoro-l-tryptophan
<220> FEATURE:
<221> NAME/KEY: MOD_RES
<222> LOCATION: (13)..(13)
<223> OTHER INFORMATION: amidation

<400> SEQUENCE: 18

Ile Cys Val Trp Gln Asp Trp Gly Ala His Arg Cys Thr
1               5                   10

<210> SEQ ID NO 19
<211> LENGTH: 13
<212> TYPE: PRT
<213> ORGANISM: Artificial sequence
```

```
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (7)..(7)
<223> OTHER INFORMATION: 5-fluoro-l-tryptophan
<220> FEATURE:
<221> NAME/KEY: MOD_RES
<222> LOCATION: (13)..(13)
<223> OTHER INFORMATION: amidation

<400> SEQUENCE: 19

Ile Cys Val Trp Gln Asp Trp Gly Ala His Arg Cys Thr
1               5                   10

<210> SEQ ID NO 20
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 5-fluoro-l-tryptophan
<220> FEATURE:
<221> NAME/KEY: MOD_RES
<222> LOCATION: (7)..(7)
<223> OTHER INFORMATION: 5-fluoro-l-tryptophan
<220> FEATURE:
<221> NAME/KEY: MOD_RES
<222> LOCATION: (13)..(13)
<223> OTHER INFORMATION: amidation

<400> SEQUENCE: 20

Ile Cys Val Trp Gln Asp Trp Gly Ala His Arg Cys Thr
1               5                   10

<210> SEQ ID NO 21
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 5-methoxytryptophan
<220> FEATURE:
<221> NAME/KEY: MOD_RES
<222> LOCATION: (13)..(13)
<223> OTHER INFORMATION: amidation

<400> SEQUENCE: 21
```

Ile Cys Val Trp Gln Asp Trp Gly Ala His Arg Cys Thr
1               5                   10

<210> SEQ ID NO 22
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 5-methyltryptophan
<220> FEATURE:
<221> NAME/KEY: MOD_RES
<222> LOCATION: (13)..(13)
<223> OTHER INFORMATION: amidation

<400> SEQUENCE: 22

Ile Cys Val Trp Gln Asp Trp Gly Ala His Arg Cys Thr
1               5                   10

<210> SEQ ID NO 23
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 1-methyltryptophan
<220> FEATURE:
<221> NAME/KEY: MOD_RES
<222> LOCATION: (13)..(13)
<223> OTHER INFORMATION: amidation

<400> SEQUENCE: 23

Ile Cys Val Trp Gln Asp Trp Gly Ala His Arg Cys Thr
1               5                   10

<210> SEQ ID NO 24
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 1-methyltryptophan
<220> FEATURE:

```
<221> NAME/KEY: MOD_RES
<222> LOCATION: (7)..(7)
<223> OTHER INFORMATION: 5-fluoro-l-typtophan
<220> FEATURE:
<221> NAME/KEY: MOD_RES
<222> LOCATION: (13)..(13)
<223> OTHER INFORMATION: amidation

<400> SEQUENCE: 24

Ile Cys Val Trp Gln Asp Trp Gly Ala His Arg Cys Thr
1               5                   10

<210> SEQ ID NO 25
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 1-formyltryptophan
<220> FEATURE:
<221> NAME/KEY: MOD_RES
<222> LOCATION: (13)..(13)
<223> OTHER INFORMATION: amidation

<400> SEQUENCE: 25

Ile Cys Val Trp Gln Asp Trp Gly Ala His Arg Cys Thr
1               5                   10

<210> SEQ ID NO 26
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Ile, Val, Leu, Ac-Ile, Ac-Val,
      Ac-Leu or Gly
<220> FEATURE:
<221> NAME/KEY: DISULFID
<222> LOCATION: (2)..(12)
<220> FEATURE:
<221> NAME/KEY: VARIANT
<222> LOCATION: (4)..(4)
<223> OTHER INFORMATION: Xaa is Trp or an analog of Trp
<220> FEATURE:
<221> NAME/KEY: VARIANT
<222> LOCATION: (7)..(7)
<223> OTHER INFORMATION: Xaa is Trp or an analog of Trp
<220> FEATURE:
<221> NAME/KEY: VARIANT
<222> LOCATION: (9)..(9)
<223> OTHER INFORMATION: Xaa is His, Ala, Phe or Trp
<220> FEATURE:
<221> NAME/KEY: VARIANT
<222> LOCATION: (13)..(13)
<223> OTHER INFORMATION: Xaa is L-Thr, D-Thr, Ile, Val, Gly, Ala or
      Asn

<400> SEQUENCE: 26

Xaa Cys Val Xaa Gln Asp Xaa Gly Xaa His Arg Cys Xaa
1               5                   10
```

```
<210> SEQ ID NO 27
<211> LENGTH: 15
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: 5-hydroxytryptophan
<220> FEATURE:
<221> NAME/KEY: MOD_RES
<222> LOCATION: (8)..(8)
<223> OTHER INFORMATION: 5-hydroxytryptophan

<400> SEQUENCE: 27

Gly Ile Cys Val Trp Gln Asp Trp Gly Ala His Arg Cys Thr Asn
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: 7-aza-tryptophan
<220> FEATURE:
<221> NAME/KEY: MOD_RES
<222> LOCATION: (8)..(8)
<223> OTHER INFORMATION: 7-aza-tryptophan

<400> SEQUENCE: 28

Gly Ile Cys Val Trp Gln Asp Trp Gly Ala His Arg Cys Thr Asn
1               5                   10                  15

<210> SEQ ID NO 29
<211> LENGTH: 45
<212> TYPE: DNA
<213> ORGANISM: Artificial sequence
<220> FEATURE:
<223> OTHER INFORMATION: synthetic sequence

<400> SEQUENCE: 29
atttgcgttt ggcaggattg gggtgcgcac cgttgcacca attaa             45

<210> SEQ ID NO 30
<211> LENGTH: 37
<212> TYPE: DNA
<213> ORGANISM: Artificial sequence
<220> FEATURE:
<223> OTHER INFORMATION: synthetic sequence

<400> SEQUENCE: 30
ggtggtgctc ttccaacggt atttgcgttt ggcagga                      37

<210> SEQ ID NO 31
<211> LENGTH: 35
<212> TYPE: DNA
<213> ORGANISM: Artificial sequence
<220> FEATURE:
<223> OTHER INFORMATION: synthetic sequence
```

-continued

<400> SEQUENCE: 31
ttggggtgcg caccgttgca ccaattaact gcagg                      35

<210> SEQ ID NO 32
<211> LENGTH: 23
<212> TYPE: DNA
<213> ORGANISM: Artificial sequence
<220> FEATURE:
<223> OTHER INFORMATION: synthetic sequence

<400> SEQUENCE: 32
caacgtggtt aattgacgtc cgc                                   23

<210> SEQ ID NO 33
<211> LENGTH: 33
<212> TYPE: DNA
<213> ORGANISM: Artificial sequence
<220> FEATURE:
<223> OTHER INFORMATION: synthetic sequence

<400> SEQUENCE: 33
cataaacgca aaccgtccta accccacgcg tgg                        33

<210> SEQ ID NO 34
<211> LENGTH: 18
<212> TYPE: DNA
<213> ORGANISM: Artificial sequence
<220> FEATURE:
<223> OTHER INFORMATION: synthetic sequence

<400> SEQUENCE: 34
cgcctgcagt taattggt                                         18

<210> SEQ ID NO 35
<211> LENGTH: 18
<212> TYPE: DNA
<213> ORGANISM: Artificial sequence
<220> FEATURE:
<223> OTHER INFORMATION: synthetic sequence

<400> SEQUENCE: 35
ggtggtgctc ttccaacg                                         18

<210> SEQ ID NO 36
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 1-methyltryptophan
<220> FEATURE:
<221> NAME/KEY: MOD_RES
<222> LOCATION: (14)..(14)
<223> OTHER INFORMATION: pegylated

<400> SEQUENCE: 36

Ile Cys Val Trp Gln Asp Trp Gly Ala His Arg Cys Thr Lys

```
1               5                   10

<210> SEQ ID NO 37
<211> LENGTH: 11
<212> TYPE: PRT
<213> ORGANISM: Artificial sequence
<220> FEATURE:
<223> OTHER INFORMATION: synthetic sequence

<400> SEQUENCE: 37

Asp Ile Cys Leu Pro Arg Trp Gly Cys Leu Trp
1               5                   10

<210> SEQ ID NO 38
<211> LENGTH: 18
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION

<400> SEQUENCE: 38

Arg Leu Ile Glu Asp Ile Cys Leu Pro Arg Trp Gly Cys Leu Trp Glu
1               5                   10                  15

Asp Asp

<210> SEQ ID NO 39
<211> LENGTH: 31
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 1-methyltryptophan
<220> FEATURE:
<221> NAME/KEY: DISULFID
<222> LOCATION: (20)..(26)

<400> SEQUENCE: 39

Ile Cys Val Trp Gln Asp Trp Gly Ala His Arg Cys Thr Arg Leu Ile
1               5                   10                  15

Glu Asp Ile Cys Leu Pro Arg Trp Gly Cys Leu Trp Glu Asp Asp
            20                  25                  30
```

POTENT COMPSTATIN ANALOGS

This claims benefit of U.S. Provisional Application No. 60/740,205, filed Nov. 28, 2005, the entire contents of which are incorporated by reference herein.

GOVERNMENT SUPPORT

Pursuant to 35 U.S.C. §202(c), it is acknowledged that the United States government may have certain rights in the invention described herein, which was made in part with funds from the National Institutes of Health under Grant No. GM 62134.

FIELD OF THE INVENTION

This invention relates to activation of the complement cascade in the body. In particular, this invention provides peptides and peptidomimetics capable of binding the C3 protein and inhibiting complement activation.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

The complement system is the first line of immunological defense against foreign pathogens. Its activation through the classical, alternative or lectin pathways leads to the generation of anaphylatoxic peptides C3a and C5a and formation of the C5b-9 membrane attack complex. Complement component C3 plays a central role in activation of all three pathways. Activation of C3 by complement pathway C3 convertases and its subsequent attachment to target surface leads to assembly of the membrane attack complex and ultimately to damage or lysis of the target cells. C3 is unique in that it possesses a rich architecture that provides a multiplicity of diverse ligand binding sites that are important in immune surveillance and immune response pathways.

Inappropriate activation of complement may lead to host cell damage. Complement is implicated in several disease states, including various autoimmune diseases, and has been found to contribute to other clinical conditions such as adult respiratory syndrome, heart attack, rejection following xenotransplantation and burn injuries. Complement-mediated tissue injury has also been found to result from bioincompatibility situations such as those encountered in patients undergoing dialysis or cardiopulmonary bypass.

Complement-mediated tissue injuries are directly mediated by the membrane attack complex, and indirectly by the generation of C3a and C5a. These peptides induce damage through their effects on various cells, including neutrophils and mast cells. In vivo, regulation of complement at the C3 and C5 activation steps is provided by both plasma and membrane proteins. The plasma protein inhibitors are factor H and C4-binding protein, and the regulatory membrane proteins located on cell surfaces are complement receptors 1 (CR1), decay-accelerating factor (DAF), and membrane cofactor protein (MCP). These proteins inhibit the C3 and C5 convertases (multi-subunit proteases), by promoting dissociation of the multisubunit complexes and/or by inactivating the complexes through proteolysis (catalyzed by factor I). Several pharmacological agents that regulate or modulate complement activity have been identified by in vitro assay, but most have been shown in vivo to be of low activity or toxic.

To date, there are no inhibitors of complement activation approved for use in the clinic, though certain candidates for clinical use exist, specifically, a recombinant form of complement receptor 1 known as soluble complement receptor 1 (sCR1) and a humanized monoclonal anti-C5 antibody (5G1.1-scFv). Both of these substances have been shown to suppress complement activation in in vivo animal models (Kalli K R et al., 1994; and, Wang et al., 1996). However, each substance possesses the disadvantage of being a large molecular weight protein (240 kDa and 26 kDa, respectively) that is difficult to manufacture and must be administered by infusion. Accordingly, recent research has emphasized the development of smaller active agents that are easier to deliver, more stable and less costly to manufacture.

U.S. Pat. No. 6,319,897 to Lambris et al. describes the use of a phage-displayed combinatorial random peptide library to identify a 27-residue peptide that binds to C3 and inhibits complement activation. This peptide was truncated to a 13-residue cyclic segment that maintained complete activity, which is referred to in the art as compstatin. Compstatin inhibits the cleavage of C3 to C3a and C3b by C3 convertases. Compstatin has been tested in a series of in vitro, in vivo, ex vivo, and in vivo/ex vivo interface experiments, and has been demonstrated to: (1) inhibit complement activation in human serum (Sahu A et al., 1996); (2) inhibit heparin/protamine-induced complement activation in primates without significant side effects (Soulika A M et al., 2000); (3) prolong the lifetime of a porcine-to-human xenograft perfused with human blood (Fiane A E et al., 1999a; Fiane A E et al., 1999b; and, Fiane A E et al., 2000); (4) inhibit complement activation in models of cardio-pulmonary bypass, plasmapheresis, and dialysis extra-corporeal circuits (Nilsson B et al., 1998); and (5) possess low toxicity (Furlong S T et al., 2000).

Compstatin is a peptide comprising the sequence ICVVQDWGHHRCT-NH$_2$ (SEQ ID NO:1), where Cys2 and Cys12 form a disulfide bridge. Its three-dimensional structure was determined using homonuclear 2D NMR spectroscopy in combination with two separate experimentally restrained computational methodologies. The first methodology involved distance geometry, molecular dynamics, and simulated annealing (Morikis D et al., 1998; WO99/13899) and the second methodology involved global optimization (Klepeis et al., *J. Computational Chem.*, 20:1344-1370, 1999). The structure of compstatin revealed a molecular surface that comprises of a polar patch and a non-polar patch. The polar part includes a Type I β-turn and the non-polar patch includes the disulfide bridge. In addition, a series of analogs with alanine replacements (an alanine scan) was synthesized and tested for activity, revealing that the four residues of the β-turn and the disulfide bridge with the surrounding hydrophobic cluster play important roles in compstatin's inhibitory activity (Morikis et al., 1998; WO99/13899).

Using a complement activity assay comprising measuring alternative pathway-mediated erythrocyte lysis, the IC$_{50}$ of compstatin has been measured as 12 µM. Certain of the analogs previously tested have demonstrated activity equivalent to or greater than that of compstatin. Published International application No. WO2004/026328 discloses compstatin analogs and mimetics with variations at the N- and C-termini, and at positions 4 and 9, which imparted improved activity in the aforementioned assay. Improvements of up to 99-fold over compstatin were reported for certain analogs (see also, Mallik et al., 2005). The development of compstatin analogs or mimetics with even greater activity would constitute a significant advance in the art.

SUMMARY OF THE INVENTION

The present invention provides analogs and mimetics of the complement-inhibiting peptide, compstatin (HOOC—ICVVQDWGHHRCT-NH$_2$; SEQ ID NO:1), which have improved complement-inhibiting activity as compared to compstatin.

In one aspect, the invention features a compound that inhibits complement activation, which comprises a peptide having a sequence:

Xaa1-Cys-Val-Xaa2-Gln-Asp-Xaa3-Gly-Xaa4-His-Arg-Cys-Xaa5 (SEQ ID NO:26); wherein:

Xaa1 is Ile, Val, Leu, Ac-Ile, Ac-Val, Ac-Leu or a dipeptide comprising Gly-Ile;

Xaa2 is Trp or an analog of Trp, wherein the analog of Trp has increased hydrophobic character as compared with Trp, with the proviso that, if Xaa3 is Trp, Xaa2 is the analog of Trp;

Xaa3 is Trp or an analog of Trp comprising a chemical modification to its indole ring wherein the chemical modification increases the hydrogen bond potential of the indole ring;

Xaa4 is His, Ala, Phe or Trp;

Xaa5 is L-Thr, D-Thr, Ile, Val, Gly, a dipeptide comprising Thr-Asn, or a dipeptide comprising Thr-Ala, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond.

In certain embodiments, Xaa2 participates in a nonpolar interaction with C3. In other embodiments, Xaa3 participates in a hydrogen bond with C3. In other embodiments, Xaa2 participates in a nonpolar interaction with C3, and Xaa3 participates in a hydrogen bond with C3.

In various embodiments, the analog of Trp of Xaa2 is a halogenated tryptophan, such as 5-fluoro-1-tryptophan or 6-fluoro-1-tryptophan. In other embodiments, the Trp analog at Xaa2 comprises a lower alkoxy or lower alkyl substituent at the 5 position, e.g., 5-methoxytryptophan or 5-methyltryptophan. In other embodiments, the Trp analog at Xaa 2 comprises a lower alkyl or a lower alkenoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan.

In certain embodiments, Xaa2 comprises a lower alkenoyl or lower alkyl substituent at the 1 position of tryptophan, Xaa3 optionally comprises a halogenated tryptophan and Xaa4 comprises Alanine. In particular embodiments, Xaa2 is 1-methyltryptophan or 1-formyltryptophan and Xaa3 optionally comprises 5-fluoro-1-tryptophan. Some exemplary compounds of the invention comprise any of SEQ ID NOS: 15-25.

In some embodiments, the compound comprises a peptide produced by expression of a polynucleotide encoding the peptide. In other embodiments, the compound is produced at least in part by peptide synthesis. A combination of synthetic methods can also be used.

In certain embodiments, the compstatin analogs are, wherein the compound is PEGylated, as exemplified by the compound comprising SEQ ID NO:36.

In other embodiments, the compstatin analog further comprises an additional peptide component that extends the in vivo retention of the compound. For example, the additional peptide component can be an albumin binding peptide. One exemplary compstatin-albumin binding peptide conjugate comprises SEQ ID NO:39.

Another aspect of the invention features a compound that inhibits complement activation, comprising a non-peptide or partial peptide mimetic of SEQ ID NO:26 or any of the other sequences of analogs and conjugates described hereinabove. These non-peptide or partial peptide mimetics are designed to bind C3 and inhibit complement activation with at least 100-fold greater activity than does a peptide comprising SEQ ID NO: 1 under equivalent assay conditions.

The compstatin analogs, conjugates and mimetics of the invention are of practical utility for any purpose for which compstatin itself is utilized, as known in the art and described in greater detail herein. Certain of these uses involve the formulation of the compounds into pharmaceutical compositions for administration to a patient. Such formulations may comprise pharmaceutically acceptable salts of the compounds, as well as one or more pharmaceutically acceptable diluents, carriers excipients, and the like, as would be within the purview of the skilled artisan.

Various features and advantages of the present invention will be understood by reference to the detailed description, drawings and examples that follow.

DETAILED DESCRIPTION OF ILLUSTRATIVE EMBODIMENTS

Figure 1:
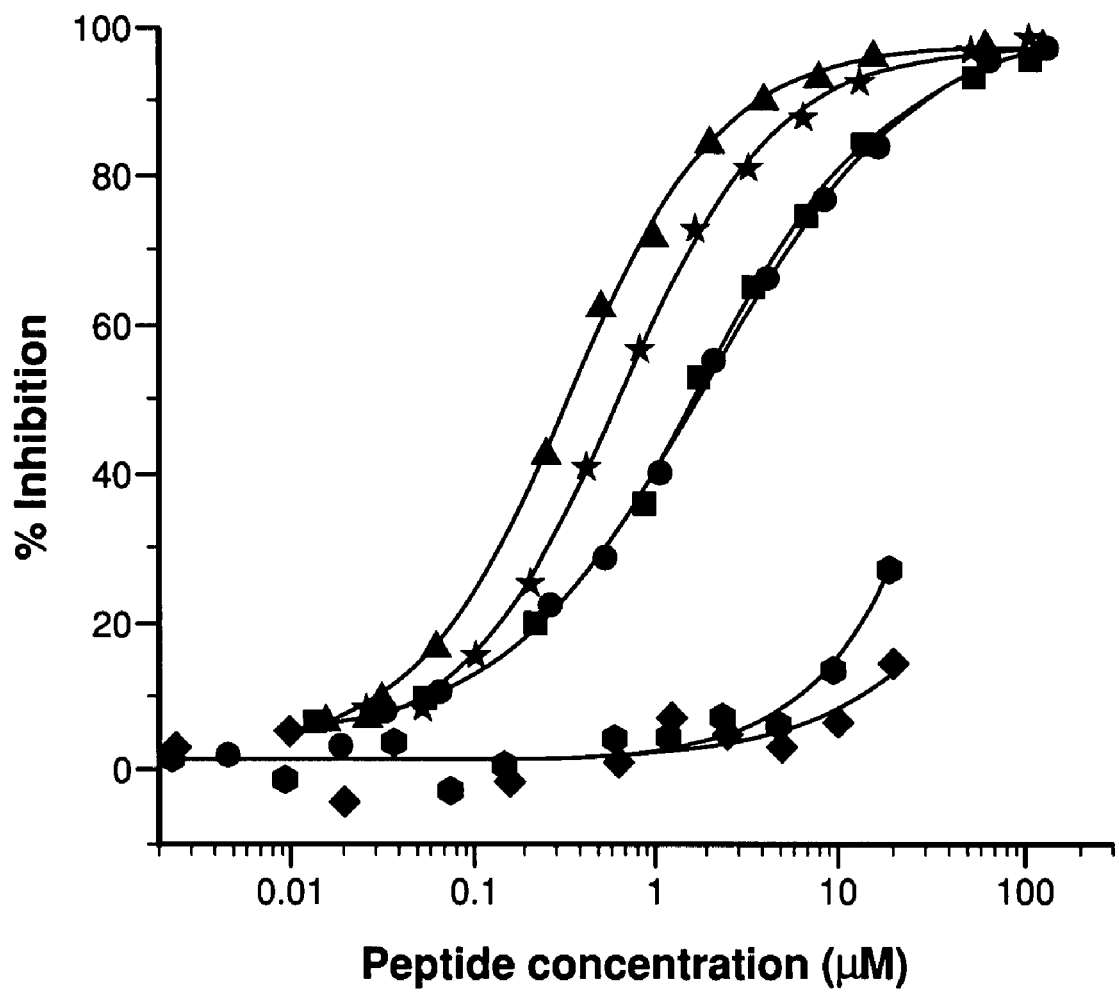
FIG. 1. Activity of expressed compstatin and its analogs. Plots of percent complement inhibition versus peptide concentration for Ac-V4W/H9A (SEQ ID NO:5) (squares) and expressed compstatin with tryptophan (SEQ ID NO: 15) (circles), 5-fluoro-tryptophan (SEQ ID NO:16) (triangles), 6-fluoro-tryptophan (SEQ ID NO:17 (stars), 5-hydroxy-tryptophan (SEQ ID NO:27) (hexagons), 7-aza-tryptophan (SEQ ID NO: 28) (diamonds).

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Definitions

The following abbreviations may be used in the specification and examples: Ac, acetyl group; NH$_2$, amide; MALDI, matrix-assisted laser desorption ionization; TOF, time of flight; ITC, isothermal titration calorimetry; HPLC, high performance liquid chromatography; NA, not active; dT, D-threonine; 2-Nal, 2-napthylalanine; 1-Nal, 1-napthylalanine; 2-Igl, 2-indanylglycine; Dht, dihydrotryptophan; Bpa, 4-benzoyl-L-phenylalanine; 5f-1-W, 5-fluoro-1-tryptophan; 6f-1-W, 6-fluoro-1-tryptophan; 5-OH—W, 5-hydroxytryptophan; 5-methoxy-W, 5-methoxytryptophan; 5-methyl-W, 5-methyltryptophan; 1-methyl-W, 1-methyltryptophan; amino acid abbreviations use the standard three- or single-letter nomenclature, for example Trp or W for tryptophan.

The term "about" as used herein when referring to a measurable value such as an amount, a temporal duration, and the like, is meant to encompass variations of +20% or ±10%, in some embodiments ±5%, in some embodiments ±1%, and in some embodiments ±0.1% from the specified value, as such variations are appropriate to make and used the disclosed compounds and compositions.

The terms "pharmaceutically active" and "biologically active" refer to the ability of the compounds of the invention to bind C3 or fragments thereof and inhibit complement activation. This biological activity may be measured by one or more of several art-recognized assays, as described in greater detail herein.

As used herein, "alkyl" refers to an optionally substituted saturated straight, branched, or cyclic hydrocarbon having from about 1 to about 10 carbon atoms (and all combinations and subcombinations of ranges and specific numbers of carbon atoms therein), with from about 1 to about 7 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. The term "lower alkyl" refers to an optionally substituted saturated straight, branched, or cyclic hydrocarbon having from about 1 to about 5 carbon atoms (and all combinations and subcombinations of ranges and specific numbers of carbon atoms therein).

Lower alkyl groups include, but are not limited to, methyl, ethyl, n-propyl, isopropyl, n-butyl, isobutyl, t-butyl, n-pentyl, cyclopentyl, isopentyl and neopentyl.

As used herein, "halo" refers to F, Cl, Br or I.

As used herein, "alkanoyl", which may be used interchangeably with "acyl", refers to an optionally substituted a straight or branched aliphatic acylic residue having from about 1 to about 10 carbon atoms (and all combinations and subcombinations of ranges and specific numbers of carbon atoms therein), with from about 1 to about 7 carbon atoms being preferred. Alkanoyl groups include, but are not limited to, formyl, acetyl, propionyl, butyryl, isobutyryl pentanoyl, isopentanoyl, 2-methyl-butyryl, 2,2-dimethylpropionyl, hexanoyl, heptanoyl, octanoyl, and the like. The term "lower alkanoyl" refers to an optionally substituted straight or branched aliphatic acylic residue having from about 1 to about 5 carbon atoms (and all combinations and subcombinations of ranges and specific numbers of carbon atoms therein. Lower alkanoyl groups include, but are not limited to, formyl, acetyl, n-propionyl, iso-propionyl, butyryl, iso-butyryl, pentanoyl, iso-pentanoyl, and the like.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and have from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy, among others.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen at selected locations on a molecule. Exemplary substituents include, for example, halo, alkyl, cycloalkyl, aralkyl, aryl, sulfhydryl, hydroxyl (—OH), alkoxyl, cyano (—CN), carboxyl (—COOH), acyl (alkanoyl: —C(=O)R); —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term D-amino acid" refers to dextrorotatory alpha-amino acids. Unless specified otherwise, all amino acids referred to herein are L-amino acids.

"Hydrophobic" or "nonpolar" are used synonymously herein, and refer to any inter- or intra-molecular interaction not characterized by a dipole.

As used herein, "pi character" refers to the capacity of compstatin to participate in a pi bond with C3. Pi bonds result from the sideways overlap of two parallel p orbitals.

As used herein, "hydrogen bond potential" refers to the capacity of compstatin to participate in an electrostatic attraction with C3 involving electronegative moieties on the modified tryptophan residues or tryptophan analogs on compstatin and hydrogen atoms on C3. A non-limiting example of such an electronegative moiety is a fluorine atom.

"PEGylation" refers to the reaction in which at least one polyethylene glycol (PEG) moiety, regardless of size, is chemically attached to a protein or peptide to form a PEG-peptide conjugate. "PEGylated means that at least one PEG moiety, regardless of size, is chemically attached to a peptide or protein. The term PEG is generally accompanied by a numeric suffix that indicates the approximate average molecular weight of the PEG polymers; for example, PEG-8,000 refers to polyethylene glycol having an average molecular weight of about 8,000.

As used herein, "pharmaceutically-acceptable salts" refers to derivatives of the disclosed compounds wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

Description

In accordance with the present invention, information about the biological and physico-chemical characteristics of compstatin have been employed to design compstatin analogs with significantly improved activity compared to the parent compstatin peptide. In some embodiments, the analogs have at least 50-fold greater activity than does compstatin. In other embodiments, the analogs have 60-, 65-, 70-, 75-, 80-, 85-, 90-, 95-, 100-, 105-, 110-, 115-, 120-, 125-, or 130-fold or greater activity than does compstatin. In still other embodiments, the analogs have, 135-, 140-, 145-, 150-, 155-, 160-, 165-, 170-, 175-, 180-, 185-, 190-, 195-, 200-, 205-, 210-, 215-, 220-, 225-, 230-, 235-, 240-, 245-, 250-, 255-, 260-, 265-fold or greater activity than does compstatin, as compared utilizing the assays described in the examples.

Compstatin analogs synthesized in accordance with other approaches have been shown to possess somewhat improved activity as compared with the parent peptide, i.e., up to about 99-fold (Mallik, B. et al, 2005, supra; WO2004/026328). The analogs produced in accordance with the present invention possess even greater activity than either the parent peptide or analogs thereof produced to date, as demonstrated by in vitro assays as shown in the figures and in the Examples herein.

Table 1B shows amino acid sequence and complement inhibitory activities of compstatin and selected analogs with significantly improved activity. The selected analogs are referred to by specific modifications of designated positions (1-13) as compared to the parent peptide, compstatin (SEQ ID NO: 1) and to the peptides of SEQ NOS: 2-14, shown in Table 1A, which were described in WO2004/026328. The peptides of SEQ ID NOS: 15-24 are representative of modifications made in accordance with the present invention, resulting in significantly more potent compstatin analogs. As described in greater detail below, it will be understood that certain of the modifications made to tryptophan at position 4 as set forth in SEQ ID NOS: 2-13 may be combined with a tryptophan analog substitution at position 7, to form yet additional potent compstatin analogs.

TABLE 1

| Peptide | Sequence | SEQ ID NO: | Activity over compstatin |
|---|---|---|---|
| A. Compstatin and Previously Described Analogs ||||
| Compstatin | H-ICVVQDWGHHRCT-CONH2 | 1 | * |
| Ac-compstatin | Ac-ICVVQDWGHHRCT-CONH2 | 2 | 3xmore |
| Ac-V4Y/H9A | Ac-ICVYQDWGAHRCT-CONH2 | 3 | 19xmore |
| Ac-V4W/H9A —OH | Ac-ICVWQDWGAHRCT-COOH | 4 | 25xmore |
| Ac-V4W/H9A | Ac-ICVWQDWGAHRCT-CONH2 | 5 | 55xmore |
| Ac-V4W/H9A/T13dT —OH | Ac-ICVWQDWGAHRCdT-COOH | 6 | 55xmore |
| Ac-V4(2-Nal)/H9A | Ac-ICV**(2-Nal)QDWGA**HRCT-CONH2 | 7 | 99xmore |
| Ac V4(2-Nal)/H9A —OH | Ac-ICV**(2-Nal)QDWGA**HRCT-COOH | 8 | 39xmore |
| Ac V4(1-Nal)/H9A —OH | Ac-ICV**(1-Nal)QDWGA**HRCT-COOH | 9 | 30xmore |
| Ac-V4Igl/H9A | Ac-ICV(2-Igl)QDWGAHRCT-CONH2 | 10 | 39xmore |

TABLE 1-continued

| Peptide | Sequence | SEQ ID NO: | Activity over compstatin |
|---|---|---|---|
| Ac-V4Igl/H9A —OH | Ac-ICV(2-Igl)QDWGAHRCT-COOH | 11 | 37xmore |
| Ac-V4Dht/H9A —OH | Ac-ICVDhtQDWGAHRCT-COOH | 12 | 5xmore |
| Ac-V4(Bpa)/H9A —OH | Ac-ICV**(Bpa)QDWGA**HRCT-COOH | 13 | 49xmore |
| +G/V4W/H9A +AN —OH | H-GICVWQDWGAHRCTAN-COOH | 14 | 38xmore |
| B. Exemplary Analogs Described Herein ||||
| +G/V4W/H9A +N —OH | H-GICVWQDWGAHRCTN-COOH | 15 | 45xmore |
| +G/V4(5f-1-W)/W7(5f-1-W),/H9A+N —OH | H-GICV**(5f-1-W)QD(5f-1-W)GAHRCTN**-COOH | 16 | 112xmore |
| +G/V4(6f-1-W)/W7(6f-1-W)/H9A+N —OH | H-GICV**(6f-1-W)QD(6f-1-W)GAHRCTN**-COOH | 17 | 126xmore |
| Ac-V4(5f-1-W)/H9A | Ac-ICV**(5f-1-W)QDWGA**HRCT-CONH$_2$ | 18 | 31xmore |
| Ac-V4W/W7(5f-1-W)/H9A | Ac-ICVWQD**(5f-1-W)GA**HRCT-CONH$_2$ | 19 | 121xmore |
| Ac-V4(5f-1-W)/W7(5f-1-W)/H9A | Ac-ICV**(5f-1-W)QD(5f-1-W)GA**HRCT-CONH$_2$ | 20 | 161xmore |
| Ac-V4(5-methoxy-W)/H9A | AC-ICV**(5-methoxy-W)QDWGA**HRCT-CONH$_2$ | 21 | 76xmore |
| Ac-V4(5-methyl-W)/H9A | Ac-ICV**(5-methyl-W)QDWGA**HRCT-CONH$_2$ | 22 | 67xmore |
| Ac-V4(1-methyl-W)/H9A | Ac-ICV**(1-methyl-W)QDWGA**HRCT-CONH$_2$ | 23 | 264xmore |
| Ac-V4(1-methyl-W)/W7(5f-1-W)/H9A | Ac-ICV**(1-methyl-W)QD(5f-1-W)GA**HRCT-CONH$_2$ | 24 | 264xmore |
| Ac-V4(1-formyl-W)/H9A | Ac-ICV**(1-formyl-W)QDWGA**HRCT-CONH$_2$ | 25 | 264xmore |

Abbreviations used in this table are as follows:
dT = D-threonine
2-Nal = 2-napthylalanine
1-Nal = 1-napthylalanine
2-Igl = 2-indanylglycine
Dht = dihydrotryptophan
Bpa = 4-benzoyl-L-phenylalanine
5f-1-W = 5-fluoro-1-tryptophan
6f-1-W = 6-fluoro-1-tryptophan
5-OH-W = 5-hydroxytryptophan
5-methoxy-W = 5-methoxytryptophan
5-methyl-W = 5-methyltryptophan
1-methyl-W = 1-methyltryptophan
1-formyl-W = 1-formyltryptophan Modifications at the N-terminus. Acetylation of the N-terminus typically increases the complement-inhibiting activity of compstatin and its analogs, as can be seen specifically by comparing SEQ ID NO: 1 with SEQ ID NO:2. Accordingly, addition of an acyl group at the amino terminus of the peptide, including but not limited to N-acetylation, is one preferred embodiment of the invention, of particular utility when the peptides are prepared synthetically. However, it is sometimes of advantage to prepare the peptides by expression of a peptide-encoding nucleic acid molecule in a prokaryotic or eukaryotic expression system, or by in vitro transcription and translation. For these embodiments, the naturally-occurring N-terminus may be utilized. One example of a compstatin analog suitable for expression in vitro or in vivo is represented by SEQ ID NOS:15-17, wherein the acetyl group is replaced by unmodified glycine at the N-terminus. SEQ ID NOS:15-17, which additionally comprise modifications within the peptides and at the C-termini as discussed below, are between about 45- and about 125-fold more active than compstatin in the complement inhibition assay described herein.

Modification within the peptide. Using computational methods that the rank low lying energy sequences, it was previously determined that Tyr and Val were the most likely candidates at position 4 to support stability and activity of the peptide (Klepeis J L et al., 2003). It was disclosed in WO2004/026328 that Trp at position 4, especially combined with Ala at position 9, yields many-fold greater activity than that of the parent peptide (for example, compare activities of SEQ ID NOS: 4, 5 and 6 with those of SEQ ID NOS: 2 and 3). WO2004/026326 also disclosed that peptides comprising the tryptophan analogs 2-napthylalanine (SEQ ID NOS: 7, 8), 1-naphthylalanine (SEQ ID NO: 9), 2-indanylglycine (SEQ ID NOS: 10, 11) or dihydrotryptophan (SEQ ID NO: 12) at position 4 were all found to possess increased complement-inhibitory activity, ranging from 5-fold to 99-fold greater than compstatin. In addition, a peptide comprising the phenylalanine analog, 4-benzoyl-L-alanine, at position 4 (SEQ ID NO: 13) possessed 49-fold greater activity that did compstatin.

In accordance with the present invention, peptides comprising 5-fluoro-1-tryptophan (SEQ ID NO:19) or either 5-methoxy-, 5-methyl- or 1-methyl-tryptophan, or 1-formyl-tryptophan (SEQ ID NOS: 21, 22, 23 and 25, respectively) at position 4 possess 31-264-fold greater activity than does compstatin. Incorporation of 1-methyl- or 1-formyl-tryptophan increased the activity and the binding affinity the most in comparison to other analogs. It is believed that an indole 'N'-mediated hydrogen bond is not necessary at position 4 for the binding and activity of compstatin. The absence of this hydrogen bond or reduction of the polar character by replacing hydrogen with lower alkyl, alkanoyl or indole nitrogen at position 4 enhances the binding and activity of compstatin. Without intending to be limited to any particular theory or mechanism of action, it is believed that a hydrophobic interaction or effect at position 4 strengthens the interaction of compstatin with C3. Accordingly, modifications of Trp at position 4 (e.g., altering the structure of the side chain according to methods well known in the art), or substitutions of Trp analogs that maintain or enhance the aforementioned hydrophobic interaction are contemplated in the present invention to produce analogs of compstatin with even greater activity. Such analogs are well known in the art and include, but are not limited to the analogs exemplified herein, as well as unsubstituted or alternatively substituted derivatives thereof. Examples of suitable analogs may be found by reference to the following publications, and many others: Beene, et al. (2002) Biochemistry 41: 10262-10269 (describing, inter alia, singly- and multiply-halogenated Trp analogs); Babitzky & Yanofsky (1995) J. Biol. Chem. 270: 12452-12456 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Trp analogs may be introduced into the compstatin peptide by in vitro or in vivo expression, or by peptide synthesis, as known in the art and described in greater detail in the examples.

In certain embodiments, Trp at position 4 of compstatin is replaced with an analog comprising a 1-alkyl substituent, more particularly a lower alkyl (e.g., $C_1$-$C_5$) substitutent as defined above. These include, but are not limited to, N($\alpha$) methyl tryptophan and 5-methyltryptophan. In other embodiments, Trp at position 4 of compstatin is replaced with an analog comprising a 1-alkanoyl substituent, more particularly a lower alkanoyl (e.g., $C_1$-$C_5$) substituent as defined above. In addition to exemplified analogs, these include but are not limited to 1-acetyl-L-tryptophan and L-β-homotryptophan.

Thermodynamic experiments showed that incorporation of 5-fluoro-1-tryptophan at position 7 in compstatin increased enthalpy of the interaction between compstatin and C3, relative to wildtype compstatin, whereas incorporation of 5-fluoro-tryptophan at position 4 in compstatin decreased the enthalpy of this interaction. Without intending to be bound to any particular mechanism, the former results indicate that replacement of indole hydrogens with a fluorine atom on a Trp residue at position 7 of compstatin can strengthen hydrogen bonding potential of the indole ring, introduce new hydrogen bonding potential, or mediate an interaction with C3 through a water molecule at the binding interface. (Katragadda M et al., 2004). Hence, modifications of Trp at position 7 (e.g., altering the structure of the side chain according to methods well known in the art), or substitutions of Trp analogs that maintain or enhance the aforementioned hydrogen bonding potential, or mediate an interaction with C3 through a water molecule at the binding interface, are contemplated in the present invention to produce analogs with even greater activity. In certain embodiments, Trp analogs whose indole rings have modifications that result in increased hydrogen bonding potential or mediate an interaction with C3 through a water molecule at the binding interface may be introduced into position 7 of the compstatin peptide by in vitro or in vivo expression, or by peptide synthesis. A peptide comprising the tryptophan analog 5-fluoro-tryptophan (SEQ ID NO:19) at position 7 was found to possess a 121-fold increased activity as compared with compstatin.

In another embodiment, Trp analogs are incorporated at both positions 4 and 7 of the compstatin molecule, and His at position 9 of compstatin is optionally replaced by Ala. Thermodynamic experiments showed that incorporation of 5-fluoro-tryptophan at positions 4 and 7 in compstatin increased enthalpy of the interaction between compstatin and C3, relative to wildtype compstatin. Accordingly, modifications of Trp at positions 4 and 7 (e.g., altering the structure of the side chain according to methods well known in the art), or substitutions of Trp analogs that maintain or enhance the aforementioned hydrophobic interaction with C3 via position 4 and maintain or enhance the aforementioned hydrogen bonding potential with C3 via position 7, or interaction with C3 through a water molecule at the binding interface via position 7, are contemplated in the present invention to produce compstatin analogs with even greater activity. Such modified Trp or Trp analogs may be introduced into the compstatin peptide at positions 4 and 7 by in vitro or in vivo expression, or by peptide synthesis. Peptides comprising tryptophan analogs 5-fluoro-tryptophan (SEQ. ID. NO: 16) and comprising tryptophan analogs 6-fluoro-tryptophan (SEQ. ID. NO: 17) at positions 4 and 7 were found to possess significantly increased activity over compstatin, ranging from a 112- to a 264-fold increase in activity. In addition, peptides comprising the tryptophan analog 1-methyl-tryptophan at position 4 and 5-fluoro-tryptophan at position 7 (SEQ ID NO: 24) were found to possess a 264-fold increase in activity relative to compstatin.

Modifications at the carboxy terminus. Peptides produced by synthetic methods are commonly modified at the carboxy terminus to comprise an amide instead of an acid; this common modification can be seen in Table 1 in compstatin (SEQ ID NO:1) and several analogs. Indeed, in some instances, it has been determined that the terminal amide-containing peptides possess greater activity than do the terminal acid-containing peptides (compare, for example, SEQ ID NOS: 5 and 7 with SEQ ID NOS: 4 and 8, respectively). Accordingly, one preferred embodiment of the invention utilizes the C-terminal amide modification. However, some circumstances favor the use of an acid at the C-terminus. Such circumstances include, but are not limited to solubility considerations and the expression of the peptides in vitro or in vivo from peptide-encoding nucleic acid molecules.

The carboxy-terminal residue of compstatin is threonine. In some embodiments of the present invention, the C-terminal threonine is replaced by one or more naturally-occurring amino acids or analogs. For example, the peptide having SEQ ID NO:6 comprises D-threonine instead of L-threonine, and further possesses a COOH group at the C-terminus. This peptide shows activity equal to that of peptide SEQ ID NO:5, comprising L-threonine and $CONH_2$ at the C-terminus. Further, Ile has been substituted for Thr at position 13, to obtain a peptide with 21-fold greater activity than that of compstatin. In addition, the peptides of SEQ ID NOS: 14-17, which comprise a C-terminal peptide extension of Asn, or a dipeptide extension of Ala-Asn, along with a COOH at the C-terminus and a non-acetylated N-terminus, demonstrate between 38- and 126-fold greater activity than does compstatin. They are also suitable for production via a prokaryotic or eukaryotic expression system, as described in greater detail below.

The compstatin analogs of the present invention may be prepared by various synthetic methods of peptide synthesis via condensation of one or more amino acid residues, in accordance with conventional peptide synthesis methods. For example, peptides are synthesized according to standard solid-phase methodologies, such as may be performed on an Applied Biosystems Model 431A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly-known protecting groups. An example of a suitable peptide synthetic method is set forth in Example 3. Modification utilizing alternative protecting groups for peptides and peptide derivatives will be apparent to those of skill in the art.

Alternatively, certain peptides of the invention may be produced by expression in a suitable prokaryotic or eukaryotic system. For example, a DNA construct may be inserted into a plasmid vector adapted for expression in a bacterial cell (such as *E. coli*) or a yeast cell (such as *Saccharomyces cerevisiae*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The peptides of SEQ ID NOS:14-17, and others similarly designed, are suitable for production by expression of a nucleic acid molecule in vitro or in vivo. A DNA construct encoding a concatemer of the peptides, the upper limit of the concatemer being dependent on the expression system utilized, may be introduced into an in vivo expression system. After the concatemer is produced, cleavage between the C-terminal Asn and the following N-terminal G is accomplished by exposure of the polypeptide to hydrazine.

The peptides produced by gene expression in a recombinant procaryotic or eucaryotic system may be purified according to methods known in the art. Examples 1 and 2 set forth methods suitable for use in the present invention. In one embodiment, a commercially available expression/secretion system can be used, whereby the recombinant peptide is expressed and thereafter secreted from the host cell, to be easily purified from the surrounding medium.

A combination of gene expression and synthetic methods may also be utilized to produce compstatin analogs. For example, an analog can be produced by gene expression and thereafter subjected to one or more post-translational synthetic processes, e.g., to modify the N- or C-terminus or to cyclize the molecule.

The structure of compstatin is known in the art, and the structures of the foregoing analogs are determined by similar means. Once a particular desired conformation of a short peptide has been ascertained, methods for designing a peptide or peptidomimetic to fit that conformation are well known in the art. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455). Of particular relevance to the present invention, the design of peptide analogs may be further refined by considering the contribution of various side chains of amino acid residues, as discussed above (i.e., for the effect of functional groups or for steric considerations).

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of the peptides of the invention, which possess the same backbone conformational features and/or other functionalities, so as to be sufficiently similar to the exemplified peptides to inhibit complement activation.

The use of peptidomimetics for the development of high-affinity peptide analogs is well known in the art (see, e.g., Zhao B et al., 1995; Beeley, N. 1994; and, Hruby, V J 1993) Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

The compstatin analogs of the present invention can be modified by the addition of polyethylene glycol (PEG) components to the peptide. As is well known in the art, PEGylation can increase the half-life of therapeutic peptides and proteins in vivo. In one embodiment, the PEG has an average molecular weight of about 1,000 to about 50,000. In another embodiment, the PEG has an average molecular weight of about 1,000 to about 20,000. In another embodiment, the PEG has an average molecular weight of about 1,000 to about 10,000. In an exemplary embodiment, the PEG has an average molecular weight of about 5,000. The polyethylene glycol may be a branched or straight chain, and preferably is a straight chain.

The compstatin analogs of the present invention can be covalently bonded to PEG via a linking group. Such methods are well known in the art. (Reviewed in Kozlowski A. et al. 2001; see also, Harris J M and Zalipsky S, eds. Poly(ethylene glycol), Chemistry and Biological Applications, ACS Symposium Series 680 (1997)). Non-limiting examples of acceptable linking groups include an ester group, an amide group, an imide group, a carbamate group, a carboxyl group, a hydroxyl group, a carbohydrate, a succinimide group (including without limitation, succinimidyl succinate (SS), succinimidyl propionate (SPA), succinimidyl carboxymethylate (SCM), succinimidyl succinamide (SSA) and N-hydroxy succinimide (NHS)), an epoxide group, an oxycarbonylimidazole group (including without limitation, carbonyldimidazole (CDI)), a nitro phenyl group (including without limitation, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. In certain embodiments, the linking group is a succinimide group. In one embodiment, the linking group is NHS.

The compstatin analogs of the present invention can alternatively be coupled directly to PEG (i.e., without a linking group) through an amino group, a sulfhydral group, a hydroxyl group or a carboxyl group. In one embodiment, PEG is coupled to a lysine residue added to the C-terminus of compstatin.

PEGylation is one way to increase in vivo retention of therapeutic peptides and proteins. The in vivo clearance of peptides can also be reduced by linking the peptides to certain other peptides. For instance, certain albumin binding peptides display an unusually long half-life of 2.3 h when injected by intravenous bolus into rabbits (Dennis et al., 2002). A peptide of this type, fused to the anti-tissue factor Fab of D3H44 enabled the Fab to bind albumin while retaining the ability of the Fab to bind tissue factor (Nguyen et al., 2006). This interaction with albumin resulted in significantly reduced in vivo clearance and extended half-life in mice and rabbits, when compared with the wild-type D3H44Fab, comparable with those seen for PEGylated Fab molecules, immunoadhesins, and albumin fusions. As described in Example 11 herein, the inventors have synthesized a compstatin analog fused with an albumin-binding peptide and demonstrated that the fusion protein is active in inhibiting complement activation.

The complement activation-inhibiting activity of compstatin analogs, peptidomimetics and conjugates may be tested by a variety of assays known in the art. In a preferred embodiment, the assay described in Example 4 is utilized. A non-exhaustive list of other assays is set forth in U.S. Pat. No. 6,319,897, including, but not limited to, (1) peptide binding to C3 and C3 fragments; (2) various hemolytic assays; (3) measurement of C3 convertase-mediated cleavage of C3; and (4) measurement of Factor B cleavage by Factor D.

The peptides and peptidomimetics described herein are of practical utility for any purpose for which compstatin itself is utilized, as known in the art. Such uses include, but are not limited to: (1) inhibiting complement activation in the serum, tissues or organs of a patient (human or animal), which can facilitate treatment of certain diseases or conditions, including but not limited to but not limited to, age-related macular degeneration, rheumatoid arthritis, spinal cord injury, Parkinson's disease, and Alzheimer's disease; (2) inhibiting complement activation that occurs during use of artificial organs or implants (e.g., by coating or otherwise treating the artificial organ or implant with a peptide of the invention); (3) inhibiting complement activation that occurs during extracorporeal shunting of physiological fluids (blood, urine) (e.g., by coating the tubing through which the fluids are shunted with a peptide of the invention); and (4) in screening of small molecule libraries to identify other inhibitors of compstatin activation (e.g., liquid- or solid-phase high-throughput assays designed to measure the ability of a test compound to compete with a compstatin analog for binding with C3 or a C3 fragment).

The following examples are provided to describe the invention in greater detail. They are intended to illustrate, not to limit, the invention. The materials and methods set forth in Examples 1-5 were utilized to generate the results described in Examples 6-11.

EXAMPLE 1

Bacterial Expression of Compstatin

A compstatin analog with the following sequence, $NH_2$-GICVWQDWGAHRCTN-OH ("G(−1)/V4W/H9A/N14") (SEQ ID NO:15) was expressed in fusion with chitin binding domain and the DnaB intein (New England Biolabs, Beverly, Mass.). Guided by the peptide sequence and the codon usage for E. coli the following genetic code was used to generate a synthetic gene for this peptide with the following sequence:

```
                                          (SEQ ID NO: 29)
5'ATTTGCGTTTGGCAGGATTGGGGTGCGCACCGTTGCACCAATTAA3'
```

To clone the synthetic gene into the pGEM-T vector, a 5' flanking region containing a SapI site and 3' flanking region containing a PstI site were designed. To construct the synthetic gene, the four overlapping oligonucleotides shown below were designed using DnaWorks software and synthesized at Invitrogen Inc. (Carlsbad, Calif.):

```
                                       (SEQ ID NO: 30)
5'GGTGGTGCTCTTCCAACGGTATTTGCGTTTGGCAGGA3'

(SEQ ID NO: 31)
5'TTGGGGTGCGCACCGTTGCACCAATTAACTGCAGG3'

(SEQ ID NO: 32)
3'CAACGTGGTTAATTGACGTCCGC5'

(SEQ ID NO: 33)
3'CATAAACGCAAACCGTCCTAACCCCACGCGTGG5'
```

The overlapping DNA fragments were assembled by PCR as described by Stemmer et al., 1995. The resulting gene was amplified using the following primers:

```
5'CGCCTGCAGTTAATTGGT3'        (SEQ ID NO: 34)

5'GGTGGTGCTCTTCCAACG3'        (SEQ ID NO: 35)
```

The PCR-amplified fragments of compstatin were then cloned into the pGEM-T vector, and the resulting clone was digested with PstI and SapI. The Pst1-SapI fragment encoding the compstatin analog was further subcloned into the expression vector pTWIN1, which had been predigested with PstI and SapI; the sequence of the clone was verified by DNA sequencing.

To express the compstatin analog, ER2566 E. coli cells transformed with the compstatin clone were grown in SOB medium (20 g/L tryptone, 5 g/L yeast extract, 0.5 g/L NaCl, 2.5 mM KCl, 10 mM $MgCl_2$) at 37° C. When an $OD_{600}$ 0.7 was reached, expression was induced by the addition of IPTG to a final concentration of 0.3 mM, followed by an additional incubation at 37° C. for 4 hr. Cells were collected by centrifugation and lysed by sonication in buffer B1 (20 mM phosphate buffer, pH 8.5, with 500 mM NaCl and 1 mM EDTA) supplemented with 0.2% Tween-20. The cell extract was centrifuged, and the soluble fraction was applied to a chitin binding column (New England Biolabs, Beverly, Mass.) pre-equilibrated with buffer B1. The column was washed with 100 ml of buffer B1, followed by a quick wash with 3 column volumes of buffer B2 (50 mM ammonium acetate, pH 7.0). The column was incubated at room temperature for 20 hr, and the peptide was eluted with Buffer B2, lyophilized and further purified on a C18 HPLC column. The purified peptide was identified using MALDI-TOF mass spectrometry.

EXAMPLE 2

Expression of Tryptophan Analogs of Compstatin In E. coli

To express compstatin analogs containing tryptophan derivatives, the pTWIN[1]-compstatin clone was transformed into the ER2566 Trp 82 auxotroph. Expression was carried out in M9 minimal medium supplemented with 1 mM L-tryptophan as described above. Cells were grown to an $OD_{600}$ 0.8-1.0, then collected by centrifugation and resuspended in fresh minimal medium containing 2 mM of the desired tryptophan analog(s): 5-fluoro-tryptophan, 6-fluoro-tryptophan, 7-aza-tryptophan or 5-hydroxy-tryptophan. The expressed compstatin analogs were further purified as described in Example 1.

EXAMPLE 3

Peptide Synthesis

Peptide synthesis and purification was performed as described by Sahu et al., 1996; Sahu et al., 2000; and Mallik et al., 2005. Briefly, peptides were synthesized in an Applied Biosystem peptide synthesizer (model 431A) using Fmoc amide resin and standard side chain protecting groups. Peptides were cleaved from the resin by incubation for 3 hours at 22° C. with a solvent mixture containing 5% phenol, 5% thioanisole, 5% water, 2.5% ethanedithiol, and 82.5% trifluoroacetic acid (TFA). The reaction mixture was filtered through a fritted funnel, precipitated with cold ether, dissolved in 50% acetonitrile containing 0.1% TFA, and lyophilized.

The crude peptides obtained after cleavage were dissolved in 10% acetonitrile containing 0.1% TFA and purified using a reverse phase C-18 column (Waters, Milford, Mass.). Disulfide oxidation was achieved by an on-resin cyclization method using the reagent Thallium (III) trifluoroacetate. This method eliminates the dilute solution oxidation steps and subsequent time-consuming concentration through lyophilization steps prior to reverse-phase HPLC. Using this method, the multimer formation was nonexistent and a high level (~90%) of fully deprotected, oxidized or cyclized material was obtained. The identity and purity of all peptides were confirmed by laser desorption mass spectroscopy and HPLC.

For the synthesis of the 5-fluoro-tryptophan, 1-methyl-tryptophan, and 5-methyl-tryptophan analogs, Fmoc-dl-derivatives were used. Separation of the enantiomeric peptides was performed as described by Meyers et al. 1978. The dl mixture of each peptide was separated into d and l isomeric peptides on a C18 reversed-phase HPLC column using 10% acetonitrile in 0.01 M ammonium acetate, pH 4.1. The isomeric identity of the eluted peptides was determined by treating the peptides with V8 protease, followed by analysis using MALDI-TOF mass spectrometry (MicroMass TOFspec2E).

EXAMPLE 4

Complement Inhibition Assays

Inhibitory activity of compstatin and its analogs on the complement system was determined by measuring their effect on the activation of the complement system by immunocomplexes. Complement activation inhibition was assessed by measuring the inhibition of C3 fixation to ovalbumin-anti-ovalbumin complexes in normal human plasma. Microtiter wells were coated with 50 µl of ovalbumin (10 mg/ml) for 2 hr at 25° C. (overnight at 4° C.). The wells were saturated with 200 µl of 10 mg/ml BSA for 1 hr at 25° C. and then a rabbit anti-ovalbumin antibody was added to form an immunocomplex by which complement can be activated. Thirty microliters of peptides at various concentrations were added directly to each well followed by 30111 of a 1:80 dilution of human plasma. After 30 min incubation, bound C3b/iC3b was detected using a goat anti-human C3 HRP-conjugated antibody. Color was developed by adding ABTS peroxidase substrate and optical density measured at 405 nm.

The absorbance data obtained at 405 nm were translated into % inhibition based on the absorbance corresponding to 100% complement activation. The % inhibition was plotted against the peptide concentration, and the resulting data set was fit to the logistic dose-response function using Origin 7.0 software. The concentration of the peptide causing 50% inhibition of C3b/iC3b deposition was taken as the $IC_{50}$ and used to compare the activities of various peptides. $IC_{50}$ values were obtained from the fitted parameters that achieved the lowest chi-square value.

EXAMPLE 5

Isothermal Titration Calorimetry Analysis of the Interaction C3 with Compstatin and its Analogs Isothermal titration calorimetry experiments were performed using the Microcal VP-ITC calorimeter (Microcal Inc, Northampton, Mass.). Protein concentrations of 3.5-5 µM and peptide concentrations of 80-200 µM were used for these experiments. All titrations were performed in PBS (10 mM phosphate buffer with 150 mM NaCl, pH 7.4). In each experiment, the target protein, C3, was loaded into the cell, and peptide was loaded into the syringe. All experiments were performed at 25° C. and for each experiment, 2-µl peptide injections were made into the cell containing the protein. In each experiment, the raw isotherms were corrected for the heats of dilution by subtracting the isotherms representing peptide injections into the buffer. The resulting isotherms were fit to various models within the Origin 7.0 software, and the model that achieved the lowest chi square value was deemed to be appropriate for the respective dataset. Binding affinity and entropy values were plotted against log P values.

EXAMPLE 6

Role of Tryptophan in C3-Compstatin Interaction as Assessed by Bacterially Expressed Compstatin Analogs Four different tryptophan analogs that differ in the chemical nature of the indole ring were incorporated into compstatin using an intein-mediated protein expression system. Following expression, the peptides were purified in a single step with a final yield of 2 mg/L of culture. The tryptophan analogs 5-fluoro-tryptophan, 6-fluoro-tryptophan, 7-aza-tryptophan and 5-hydroxy-tryptophan were also expressed using the ER2566/Trp 82 auxotroph as indicated by the MALDI profiles, and the resulting peptides were purified to homogeneity. Native compstatin and analogs were cyclized in vivo through a disulfide bond, as evidenced by their inability to react with PHMB. All peptides were further purified on a reverse-phase C18 HPLC column.

The activity of the expressed compstatin analog G(−1)/V4W/H9A/N14 (SEQ ID NO:15) exhibited an $IC_{50}$ of 1.2 µM, which is similar to the activity observed for the Ac-V4W/H9A analog (SEQ ID NO:5). This finding indicates that the glycine located at the N-terminus of the expressed peptide plays a role similar to that of the acetyl group located at the N-terminus of the Ac-V4W/H9A analog.

All the expressed compstatin analogs except the 7-aza tryptophan analog were found to be active at the concentrations tested. However, the peptide showed different levels of activity relative to the analog, Ac-V4W/H9A (FIG. 1; Table 2).

Compstatin containing 6-fluoro-tryptophan and 5-fluoro-tryptophan as well as alanine at position 9 exhibited a 2.8 and 2.5-fold higher activity, respectively, than that of the Ac-V4W/H9A analog.

TABLE 2

Complement inhibitory activity of the expressed peptides

| Expressed peptide | SEQ ID NO: | IC$_{50}$ (μM) | Relative activity* |
|---|---|---|---|
| Ac-V4W/H9A[b] | 5 | 1.2 | 45 |
| G(−1)/V4W/H9A/N14 | 15 | 1.2 | 45 |
| G(−1)/V4(5fW)/W7(5fW)/H9A/N14 | 16 | 0.48 | 112 |
| G(−1)/V4(6fW)/W7(6fW)/H9A/N14 | 17 | 0.43 | 126 |
| G(−1)/V4(5-OH[a]—W)/W7(5-OH—W)/H9A/N14 | 27 | 33 | 1.6 |
| G(−1)/V4(7-aza-W)/W7(7-aza-W)/H9A/N14 | 28 | 122 | 0.44 |

*relative to the activity of the peptide H—I(CVVQDWGHHRC)T—NH$_2$ (compstatin, SEQ ID NO: 1)
[a]represents hydroxy
[b]synthetic peptide Without being limited to any particular mechanism, it is believed that adding fluorine atom increases the activity of the peptide by increasing the hydrophobicity of the indole ring. The incorporation of less hydrophobic tryptophan analogs 5-hydroxy tryptophan and 7-aza-tryptophan was also investigated. In contrast to the results with the 5-fluoro and 6-fluoro analogs, compstatin analogs containing 5-hydroxy-tryptophan showed 27.5-fold loss in the activity compared to the Ac-V4W/H9A analog (SEQ ID NO:5), and the peptide containing 7-aza-tryptophan showed no activity at all at the concentrations tested. 7-aza-tryptophan resembles tryptophan in molecular structure except that it has a nitrogen atom at position 7 of the indole ring as opposed to a carbon atom. The loss in activity observed upon substitution of 7-aza-tryptophan shows the relative importance of this carbon atom.

EXAMPLE 7

Role of Individual Tryptophans In C3-Compstatin Interaction

Solid-phase peptide synthesis was used to generate compstatin analogs with 5-fluoro-tryprophan incorporated selectively at position 4, position 7, or both positions 4 and 7, with alanine at position 9. Synthesis was undertaken using Fmoc-5-fluoro-dl-tryptophan. This reaction yielded an enantiomeric mixture of the peptides bearing 5-fluoro-d-tryptophan and 5-fluoro-l-tryptophan. Three different peptides were synthesized: two peptides with single substitution independently at position 4 or 7 and one peptide with substitutions at both positions 4 and 7. While a mixture of 5-fluoro-1-tryptophan and 5-fluoro-d-tryptophan analogs could occur in the case of the single substitutions, a mixture of four enantiomeric combinations was possible in the case of the double substitution. Each of the peptide mixtures was further subjected to reversed-phase HPLC to separate the peptide enantiomers. Identification of the enantiomers was carried out by digesting the peptides with V8 protease and subsequently analyzing the digested product using MALDI. V8 protease cleaves at the C-terminal side of Asp residues only when followed by an l-amino acid. Identification of cleavage products in the mass spectra indicated that the l-enantiomeric peptide eluted first followed by the d-form, where no cleavage fragments were detected.

All the peptides, containing either 5-fluoro-1-tryptophan or 5-fluoro-d-tryptophan or both, were tested for their complement inhibitory activity. The synthetic peptide substituted with 5-fluoro-1-tryptophan in both the positions showed a 2.5-fold higher activity than that of Ac-V4W/H9A (SEQ ID NO:5) (Table 3).

TABLE 3

Complement inhibitory activity of the synthetic compstatin analogs containing 5-fluoro-l-tryptophan

| Peptide | SEQ ID NO: | IC$_{50}$ (μM) | Relative activity* |
|---|---|---|---|
| Ac-V4W/H9A | 5 | 1.20 | 45 |
| Ac-V4(5f-l-W)/H9A | 18 | 1.74 | 31 |
| Ac-V4W/W7(5f-l-W)/H9A | 19 | 0.446 | 121 |
| Ac-V4(5f-l-W)/W7(5f-l-W)/H9A | 20 | 0.482 | 112 |

*relative to the activity of the peptide H—I(CVVQDWGHHRC)T—NH$_2$ (compstatin, SEQ ID NO: 1)

Figure 2:
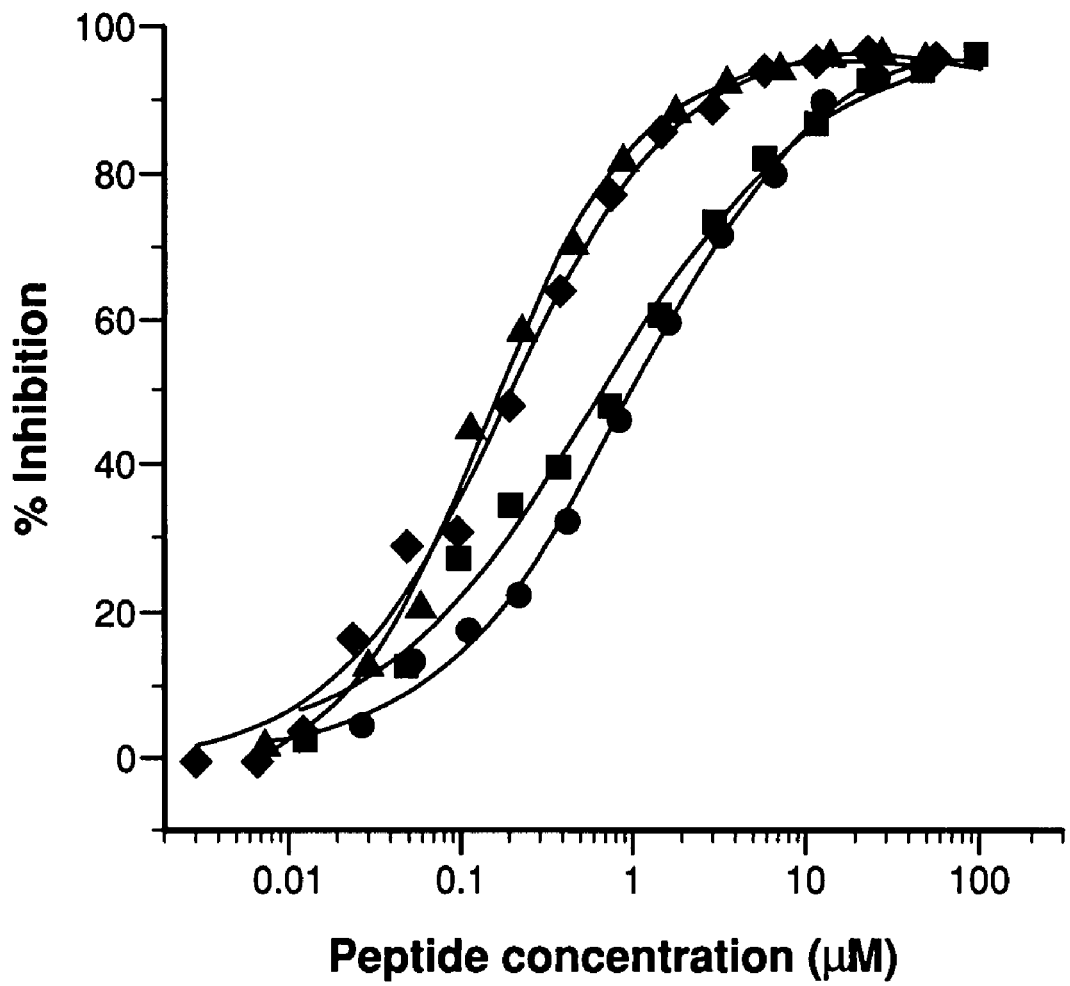
FIG. 2. Activity of synthetic compstatin analogs. Plots of percent complement inhibition versus peptide concentration for Ac-V4W/H9A (SEQ ID NO:5) (squares) and the compstatin analogs with 5-fluoro-1-tryptophan incorporation at position 4 (SEQ ID NO:18) (circles), position 7 (SEQ ID NO:19) (triangles), both positions 4 and 7 (SEQ ID NO:20) (diamonds).

Complement inhibition assays (FIG. 2; Table 3) indicated that (a) substitution of 5-fluoro-1-tryptophan at position 4 alone rendered the peptide at least 1.5 times less active than Ac-V4W/H9A (SEQ ID NO:5). Substitution of 5-fluoro-1-tryptophan at position 7 alone increased the activity 2.7-fold when compared to Ac-V4W/H9A. Substitution of 5-fluoro-1-tryptophan simultaneously at positions 4 and 7 also yielded a 2.5-fold increase in the activity relative to Ac-V4W/H9A (SEQ ID NO:5). Substitution of 5-fluoro-d-tryptophan at either position 4 or 7, or both, rendered the peptide inactive.

EXAMPLE 8

Thermodynamic Basis for the Tryptophan-Mediated Recognition of Compstatin by C3

Isothermal titration calorimetry was used to examine the binding of the peptides to C3 and investigate the thermodynamic basis for their activities. The calorimetric data obtained for the interaction of all the peptides with C3 fit to a one set of sites model with stoichiometry close to 1. It is believed that the binding of these peptides to C3 occurs in a 1:1 ratio. The thermodynamic parameters resulting from these fits are shown in Table 4. As evident from the K$_d$ values, the peptide with a single substitution of 5-fluoro-1-tryptophan at position 7 and a double substitution at positions 4 and 7 exhibited tighter binding than the Ac-V4W/H9A (SEQ ID NO:5) and the Ac-V4(5f-l-W)/H9A (SEQ ID NO:18) analogs. This finding is in agreement with the relative activities observed in the complement inhibition assay (Table 3), indicating that a binding-activity correlation exists.

All peptides bound to C3 with a negative enthalpy and positive entropy. Such binding is a characteristic of the interaction of compstatin with C3. Among all the peptides examined, the position 7-substituted Ac-V4W/W7(5f-l-W)/H9A analog (SEQ ID NO:19) exhibited a higher binding enthalpy (ΔH=−21.83, ΔΔH=−3.69) than did its wild-type counterpart. The position 4-substituted Ac-V4(5f-l-W)/H9A analog (SEQ ID NO:18) bound to C3 with an enthalpy of −16.69 kcal/mole, 1.45 kcal/mole lower than that exhibited by its wild-type counterpart.

Incorporation of 5-fluoro-tryptophan at position 4 led to a loss in enthalpy of 1.45 kcal/mole relative to that of tryptophan at this position (Table 4). Since the only difference between tryptophan and 5-fluoro-tryptophan is the fluorine atom at C5 of the indole, this loss in enthalpy can be attributed to the replacement of hydrogen with fluorine.

TABLE 4

Thermodynamic parameters for the interaction of synthetic compstatin analogs containing 5-fluoro-l-tryptophan and C3

| peptide | SEQ ID NO: | $K_d$ (μM) | ΔH | ΔΔH | -TΔS | -TΔΔS | ΔG | ΔΔG |
|---|---|---|---|---|---|---|---|---|
| Ac-V4W/H9A | 5 | 0.14 | -18.14 | 0 | 8.79 | 0 | -9.4 | 0 |
| Ac-V4(5f-l-W)/H9A | 18 | 0.15 | -16.69 | 1.45 | 7.39 | -1.4 | -9.4 | 0 |
| Ac-V4W/W7(5f-l-W)/H9A | 19 | 0.035 | -21.83 | -3.69 | 11.56 | 2.77 | -10.25 | -1 |
| Ac-V4(5f-l-W)/W7(5f-l-W)/H9A | 20 | 0.017 | -17.33 | 0.81 | 6.73 | -2.06 | -10.6 | -1.2 |

(kcal/mole)

Incorporation of 5-fluoro-tryptophan at position 7 increased the enthalpy by 3.69 kcal/mole relative to wild-type (Table 4). Without being limited to any particular mechanism, it is believed that tryptophan at position 7 is participating in an enthalpically favorable interaction such as hydrogen bonding. Replacing one of the indole hydrogens with a fluorine atom might strengthen the hydrogen bonding character of the indole NH due to the drop in $pK_a$. Alternatively, the fluorine forms a hydrogen bond as a result of its electron-donating nature, as has been demonstrated in the structure of the tetradeca (3-fluorotyrosyl)glutathione transferase.

Another explanation for the observed increase in enthalpy is that a water molecule is bridging the interaction between the fluorine atom and a hydrogen acceptor on C3, in which case two hydrogen bonds (equivalent to about 4 kcal/mole energy) need to be formed. Support for this theory comes from the decrease in entropy observed for the interaction of the position 7-substituted Ac-V4W/W7(5fW)/H9A analog (SEQ ID NO:19) relative to the wild-type analog (Table 4), a decrease that could be produced by the binding of an additional water molecule at the interface. Water-mediated interactions between fluorine atoms and other hydrogen bond acceptors have been observed in other systems.

Binding of the double-substituted analog to C3 yielded an enthalpy change of -19.85 kcal/mole, an entropy change of -9.35 kcal/mole and a free energy change of -10.5 kcal/mole. It is believed that incorporation of 5-fluoro-tryptophan simultaneously at both positions abrogates the effects of the single substitutions.

EXAMPLE 9

Additional Compstatin Analogs

Incorporation of tryptophan analogs at position 4. It was shown in Examples 5 and 6 that substitution of valine with tryptophan at position 4 of compstatin increased its activity 45-fold. To further investigate the nature of interaction mediated by residue at position 4 during the course of the binding of compstatin to C3, the tryptophan at position 4 was replaced with tryptophan analogs and 2-napthylalanine.

Figure 3A:
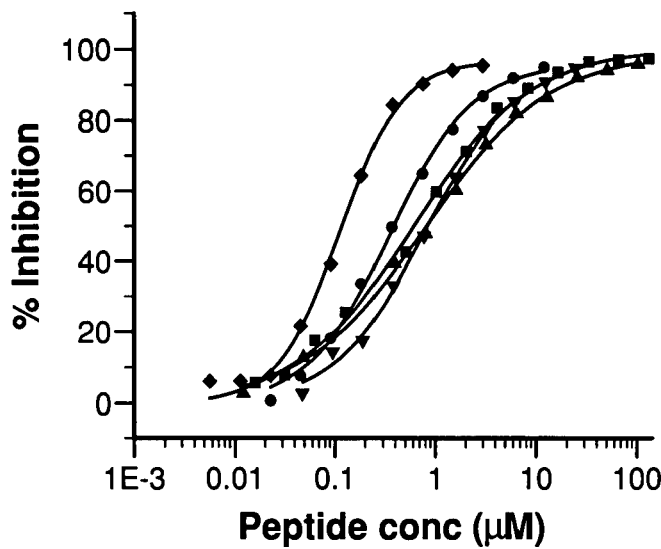
FIG. 3. Activity of additional synthetic compstatin analogs. Plots of percent complement inhibition vs. peptide concentration for (A) Ac-V4W/H9A (SEQ ID NO:5) (triangles) compared to Ac-V4(5f-1-W)/H9A (SEQ ID NO:18) (inverted triangle), Ac-V4(5-methyl-W)/H9A (SEQ ID NO:22) (circles), Ac-V4(1-methyl-W)/H9A (SEQ ID NO:23) (diamonds), Ac-V4(2-Nal)/H9A (SEQ ID NO:7) (squares); (B) Ac-V4W/H9A (SEQ ID NO:5) (triangles) compared to Ac-V4W/W7(5f-1-W)/H9A (SEQ ID NO:19) (hexagons); and, (C) wild-type compstatin (SEQ ID NO:1) (triangles) compared to Ac-V4(1-methyl-W)/W7(5f-1-W)/H9A (SEQ ID NO:24) (triangles pointing left).
Figure 3B:
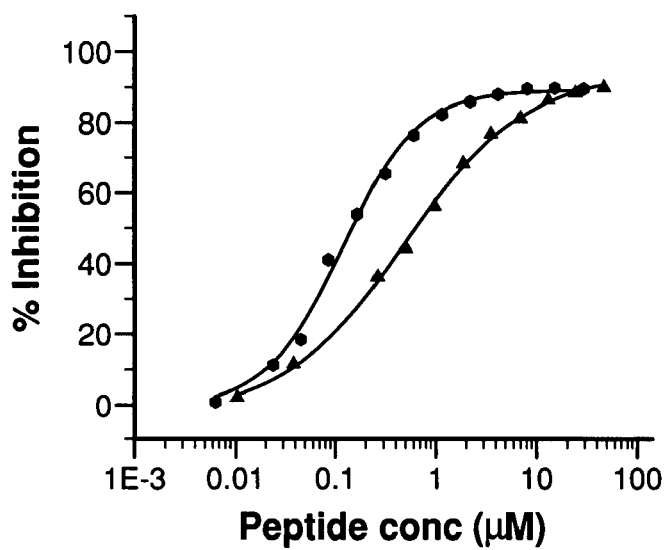
Figure 3C:
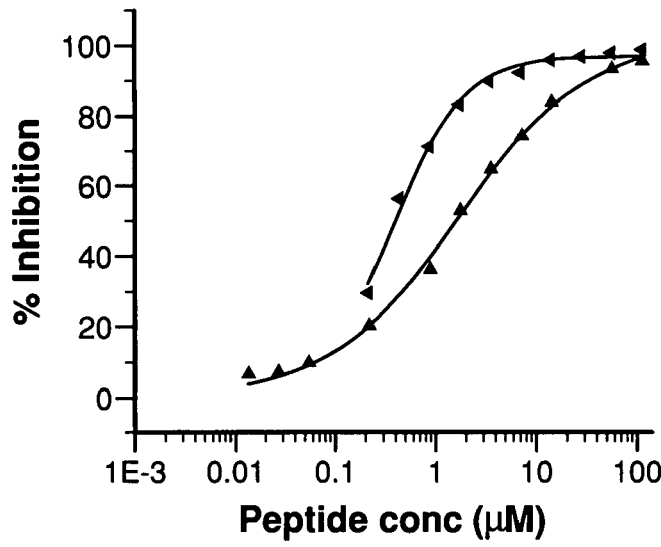
Figure 4A:
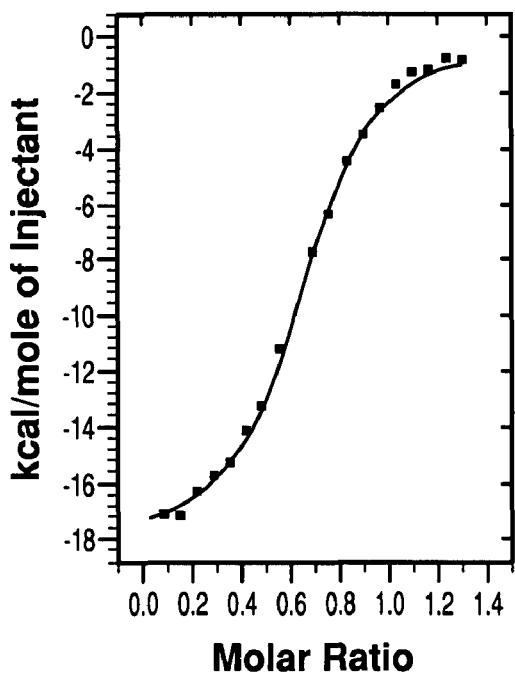
FIG. 4. Thermodynamic characterization of the interaction of additional compstatin analogs with C3. ITC data representing the binding of (A) Ac-V4W/H9A (SEQ ID NO:5); (B) Ac-V4(5f-1-W)/H9A (SEQ ID NO:18); (C) Ac-V4(5-methyl-W)/H9A (SEQ ID NO:22); (D) Ac-V4(1-methyl-W)/H9A (SEQ ID NO:23); (E) Ac-V4(2-Nal)/H9A (SEQ ID NO:7); and, (F) Ac-V4W/W7(5f-1-W)/H9A (SEQ ID NO:19) to C3. The plots were obtained by fitting the corrected raw data to "one set of sites" model in Origin 7.0
Figure 4B:
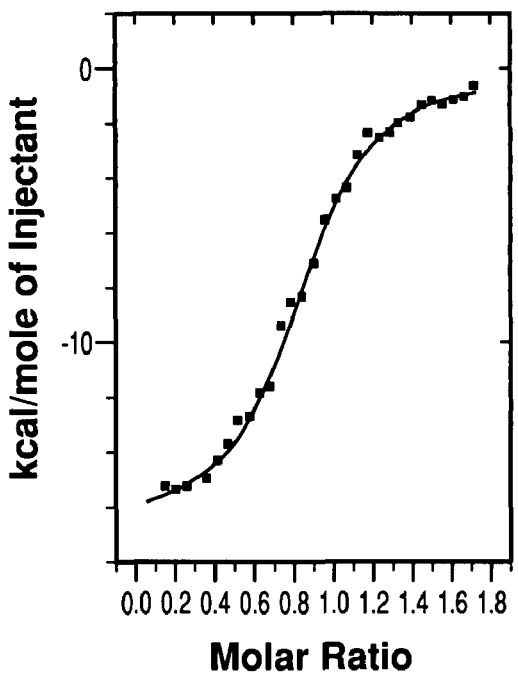
Figure 4C:
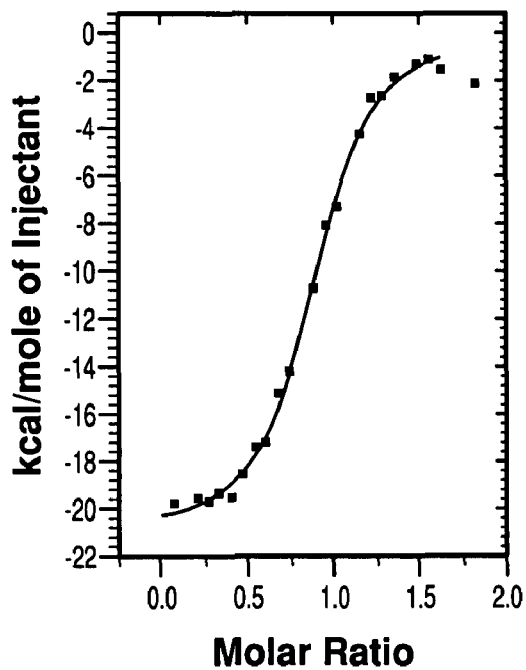
Figure 4D:
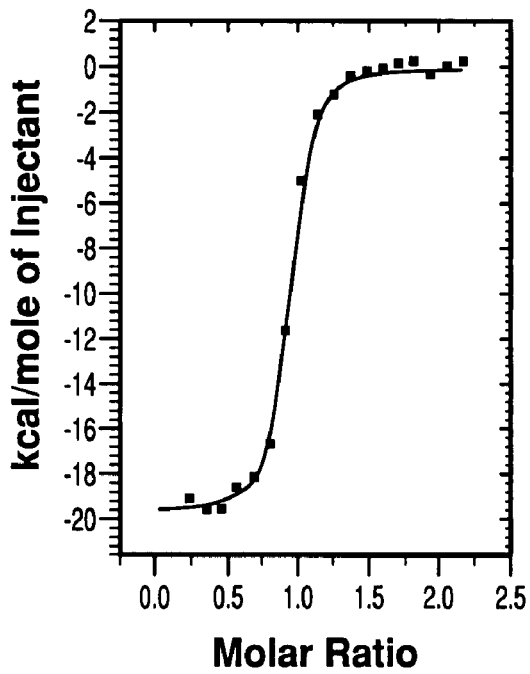
Figure 4E:
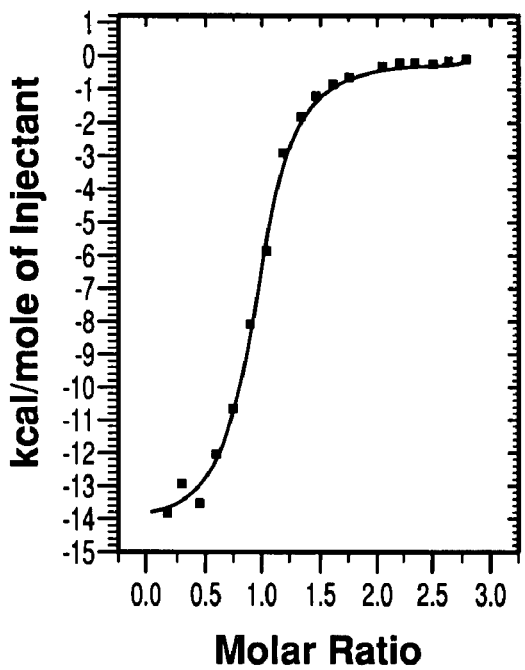
Figure 4F:
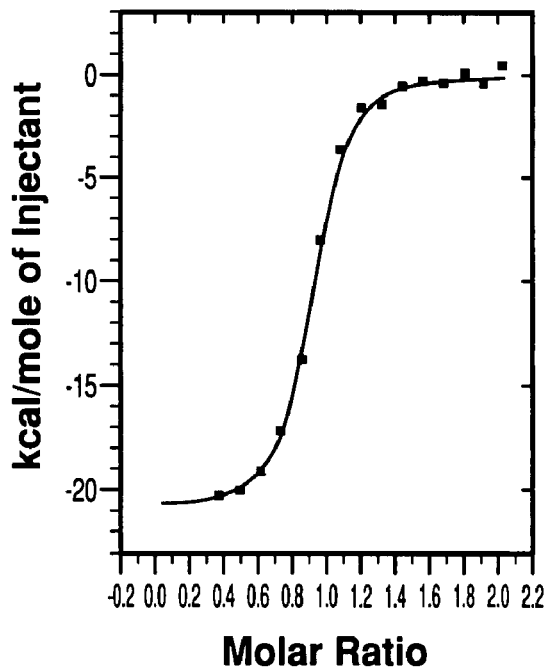
Figure 5A:
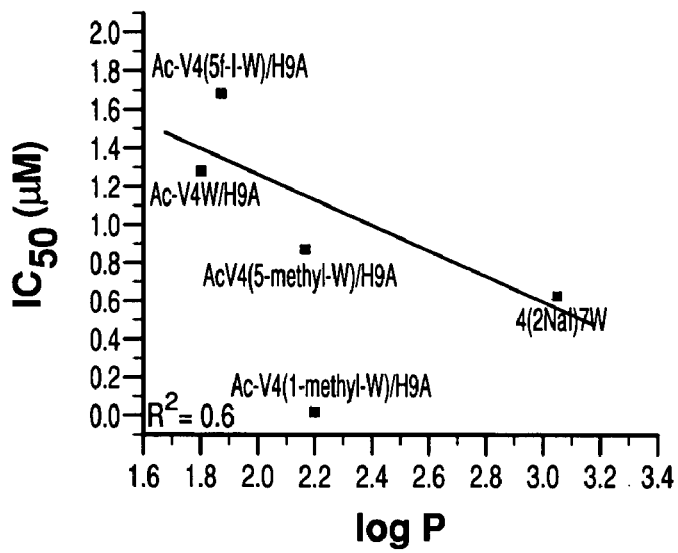
FIG. 5. Plots showing the relation between hydrophobicity of the analogs denoted by log P and the inhibitory constant (A), entropy denoted by $-T\Delta S$ (B) and the binding constant (C).
Figure 5B:
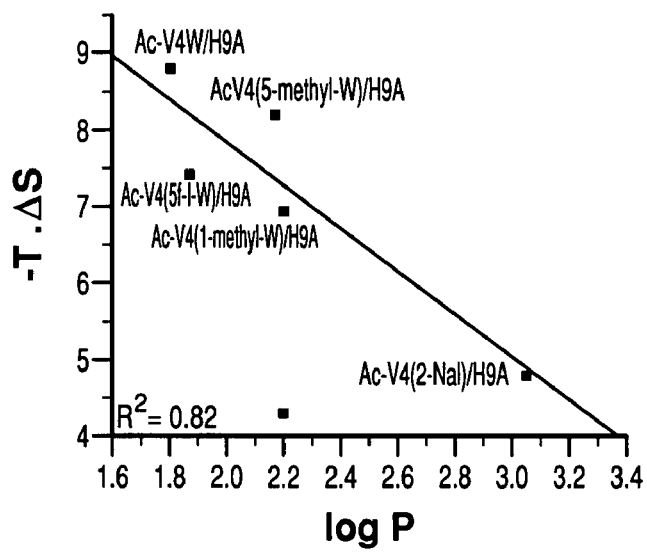
Figure 5C:
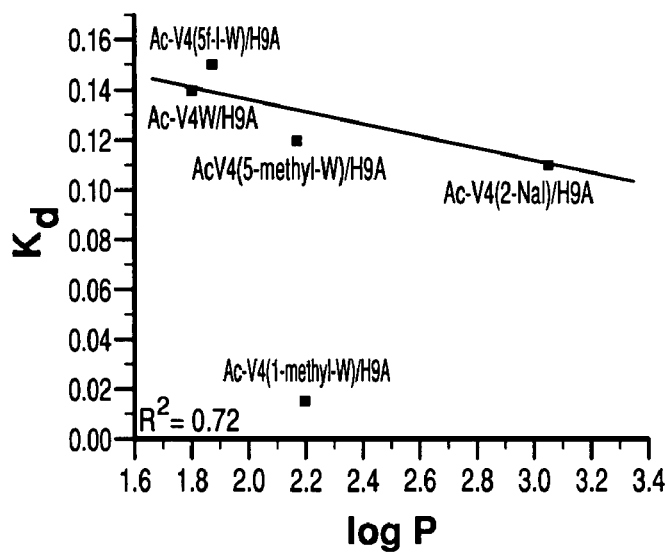

ELISA-based assays were used to test the activity of all the peptide analogs bearing tryptophan analogs at position 4 and alanine at position 9. While substitution with 1-methyl-tryptophan (Ac-V4(1-methyl-W)/H9A) (SEQ ID NO:23) and 2-naphthylalanine (Ac-V4(2-Nal)/H9A) (SEQ ID NO:7) increased the activity over compstatin 264 and 99-fold, respectively, substitution of 5-fluoro-tryptophan (Ac-V4(5f-l-W)/W7/H9A) (SEQ ID NO:18 and 5-methyl tryptophan (Ac-V4(5-methyl-W)/H9A) (SEQ ID NO:22) resulted in a lower activity; to 31 and 67-fold greater than the activity exhibited by the wild-type peptide (Table 5). FIG. 3 shows the inhibitory curves depicting the activity and Table 5 shows the $IC_{50}$ values calculated from the curves and the relative activities of the peptides in comparison to the activity of original compstatin. FIG. 5 shows inhibitory constants ($IC_{50}$) plotted against log P values of tryptophan analogs and 2-napthylalanine.

TABLE 5

Complement inhibitory activity of the compstatin analogs

| Peptide | SEQ ID NO: | $IC_{50}$ (μM) | Relative activity* |
|---|---|---|---|
| Ac-V4W/H9A | 5 | 1.20 | 45 |
| Ac-V4(5f-l-W)/7W/H9A | 18 | 1.74 | 31 |
| Ac-V4W/W7(5f-l-W)/H9A | 19 | 0.446 | 121 |
| Ac-V4(5f-l-W)/W7(5f-l-W)/H9A | 20 | 0.482 | 112 |
| Ac-V4W/7(5-methoxy W)/H9A | 29 | 0.46 | 0.5 |
| Ac-V4(5-methoxy W)/7W/H9A | 21 | 0.71 | 76 |
| Ac-V4(5-methyl W)/7W/H9A | 22 | 0.81 | 67 |
| Ac-V4(1-methyl W)/7W/H9A | 23 | 0.205 | 264 |
| Ac-V4(2-Nal)/W7/H9A | 7 | 0.545 | 99 |
| Ac-V4(1-methyl W)/W7(5f-l-W)/H9A | 24 | 0.205 | 264 |

*Relative to the activity of H—I(CVVQDWGHHRC)T—NH₂ (compstatin, SEQ ID NO: 1).

The binding of compstatin peptides was also investigated using isothermal titration calorimetry. The calorimetric data obtained for the interaction of all the peptides with C3 fit to a one set of sites model with stoichiometry close to 1 (FIG. 4). This result suggests that the binding of these peptides to C3 occurs in a 1:1 ratio. The thermodynamic parameters resulted from these fits are shown in Table 6. As evident from the $K_d$ values, Ac-V4(1-methyl-W)/H9A exhibited higher binding affinity ($K_d$=0.015 μM) compared to all other peptides having a single substitution at position 4. Plotting these values against the log P values of analogs indicates that a correlation exists between binding affinity and hydrophobic nature of the tryptophan analogs and 2-napthylalanine. As per the correlation, binding affinity increases with an increase in the hydrophobicity of the analog incorporated at position 4. This observation is consistent with the correlation shown between log P and the inhibitory constants.

TABLE 6

Thermodynamic parameters for the interaction of synthetic compstatin analogs containing 5-fluoro-l-tryptophan and C3

| Peptide | SEQ ID NO. | $K_d$ (μM) | ΔH | ΔΔH | -TΔS | -TΔΔS | ΔG | ΔΔG |
|---|---|---|---|---|---|---|---|---|
| | | | | (kcal/mole) | | | | |
| Wild-type | 1 | 0.14 | −18.14 | 0 | 8.79 | 0 | −9.4 | 0 |
| Ac-V4(5f-l-W)/H9A | 18 | 0.15 | −16.69 | 1.45 | 7.39 | −1.4 | −9.4 | 0 |
| Ac-V4(5-methyl-W)/H9A | 22 | 0.12 | −17.75 | 0.34 | 8.2 | −0.54 | −9.55 | −0.15 |
| Ac-V4(1-methyl-W)/H9A | 23 | 0.015 | −17.59 | 0.81 | 6.94 | −1.85 | −10.65 | −1.1 |
| Ac-V4(2-Nal)/H9A | 7 | 0.11 | −14.27 | 3.87 | 4.8 | −3.99 | −9.5 | −0.1 |
| Ac-V4W/W7(5f-l-W)/H9A | 19 | 0.035 | −21.83 | −3.69 | 11.56 | 2.77 | −10.25 | −0.8 |
| Ac-V4(1-methyl-W)/W7(5f-l-W)/H9A | 24 | 0.017 | −17.33 | 0.81 | 6.73 | −2.06 | −10.6 | −1.2 |

All the peptides bound to C3 with a negative enthalpy and positive entropy, suggesting that the binding is enthalpy-driven. Such binding is a characteristic of the interaction of compstatin with C3. However, the binding of these peptides is characterized by an enthalpy change lower than the wild-type, and entropy change shifted towards favorable end. FIG. 5B shows a plot of log P vs.−TΔS, which indicates that with an increase in the hydrophobicity of the analogs incorporated at position 4, the entropy is more favored thus making a positive impact on the free energy change.

Incorporation of tryptophan analogs at position 7. It was proposed in Example 7 that tryptophan at position 7 makes a hydrogen bond with a residue on C3. To examine this possibility further, tryptophan at position 7 was replaced with tryptophan analogs similar to the replacements at position 4 to elucidate the nature of interaction made by tryptophan at this position. Substitution with 5-fluoro-tryptophan (Ac-V4W/W7(5f-l-W)/H9A) (Seq ID NO:19), yielded a 121-fold more active peptide. (FIG. 3, Table 5). Substitutions of tryptophan 7 with the analog 5-methyl trp or 1-methyl trp rendered compstatin inactive (data not shown). Thus, no correlation between the activity and hydrophobicity of tryptophan analogs was observed.

The thermodynamic properties of the different Trp 7-analogs was investigated in parallel by calorimetry. (Table 6). Since no binding was detected for peptides containing either the 5-methyl trp or 1-methyl trp at position 7, the binding parameters do not exist. Only the peptide Ac-V4W/W7(5f-l-W)/H9A (SEQ ID NO:19) bound to C3. The binding affinity was 0.035 μM, which is greater that that observed for all the peptides having a Trp analog at position 4, except for the peptide Ac-V4(1-methyl-W)/H9A (SEQ ID NO:23). In contrast to the peptides having a Trp analog at position 4, Ac-V4W/W7(5f-l-W)/H9A (SEQ ID NO:19) bound to C3 with high favorable binding enthalpy change (ΔH=−21.83, ΔΔH=−3.69) and unfavorable entropy change (−TΔS=11.56, −TΔΔS=2.77), suggesting additional favorable non-covalent interactions of polar nature.

The results show that incorporation of 5-fluoro-tryptophan at position 7 results in an increase in the activity of compstatin, whereas incorporation of analogs 5-methyl-tryptophan and 1-methyl-tryptophan renders compstatin inactive. The loss of activity of compstatin upon incorporation of 1-methyl-tryptophan supports the conclusion that the hydrogen bond mediated by N—H of Trp 7 is important for the interaction of compstatin with C3. In addition, the complete loss of activity of compstatin upon incorporation of 5-methyl-tryptophan suggests that a hydrophobic amino acid is not well tolerated at position 7.

Incorporation of tryptophan analogs at both positions 4 and 7. Since the substitution of tryptophans at position 4 with 1-methyl-tryptophan and position 7 with 5-fluoro-tryptophan yielded compstatin analogs that showed a drastic increase in the activity, a compstatin analog containing substitutions at positions 4 and 7 was generated. The resulting peptide (Ac-V4(1-methyl-W)/W7(5f-l-W)/H9A) (SEQ ID NO:24) generated an inhibition curve similar to that of the single substitution with 1-methyl-tryptophan (Ac-V4(1-methyl-W)/H9A) (SEQ ID NO:23), (FIG. 3, Table 5). The binding affinity ($K_d$=0.017) observed for this peptide in the calorimeter is also similar to that of Ac-V4(1-methyl-W)/H9A (SEQ ID NO:23). These observations suggest that 5-fluoro-tryptophan has no effect at position 7 in the presence of 1-methyl-tryptophan at position 4 under these experimental conditions.

Incorporation of another tryptophan analog at position 4. To further investigate the nature of interaction mediated by residue at position 4 during the course of the binding of compstatin to C3, the tryptophan at position 4 was replaced with the tryptophan analog 1-formyl-tryptophan.

Figure 6:
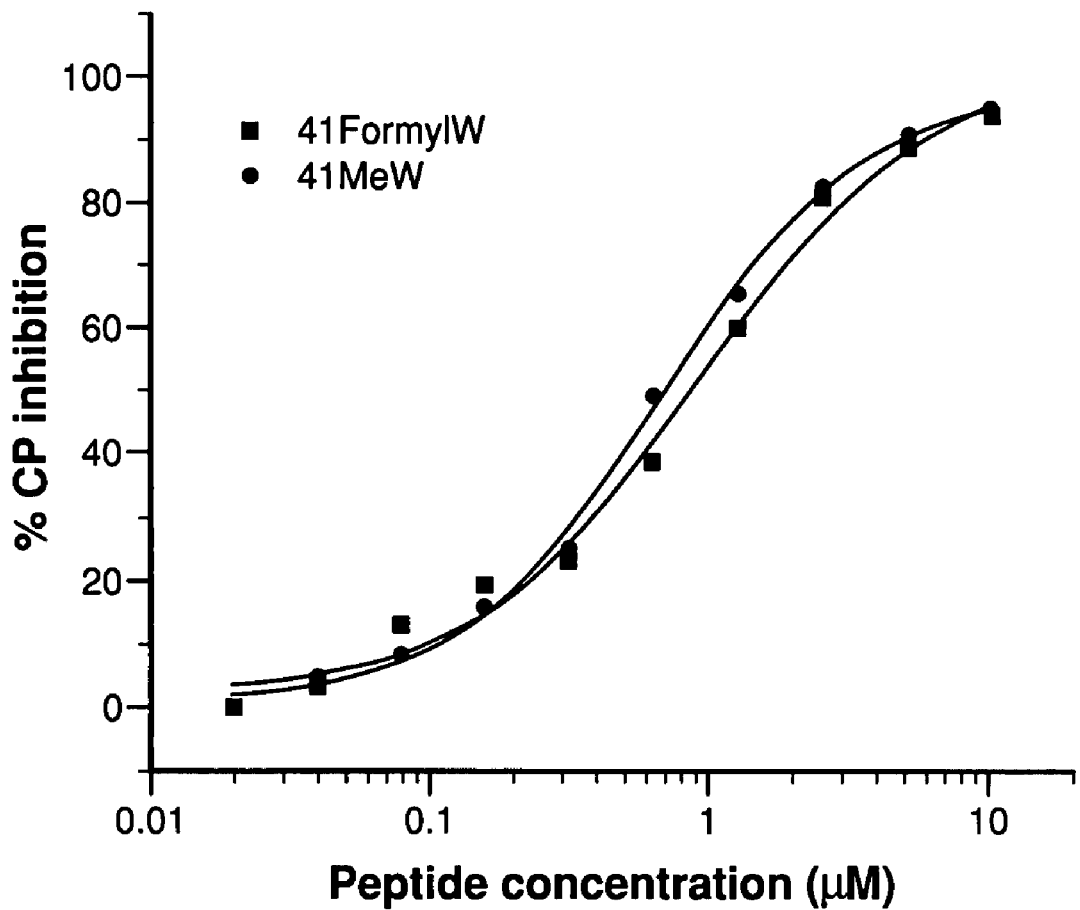
FIG. 6. Activity of an additional synthetic compstatin analog. Plots of percent complement inhibition vs. peptide concentration for Ac-V4(1-methyl-W)/H9A (SEQ ID NO:23) (circles) and Ac-V4(1-formyl-W)/H9A (SEQ ID NO:25) (squares).

FIG. 6 shows a comparison of percent complement inhibition vs. peptide concentration for Ac-V4(1-methyl-W)/H9A (SEQ ID NO:23) (circles) and Ac-V4(1-formyl-W)/H9A (SEQ ID NO:25). As can be seen, the 1-formyl-W analog was essentially identical to the 1-methyl-W analog in its complement inhibition activity.

EXAMPLE 10

PEGylation of Compstatin Analog

A prolonged half-life of compstatin is advantageous for its use in chronic treatments. Extending the half-life of tested therapeutic peptides has been achieved in several instances through PEGylation (see Veronese et al., 2001), as PEG has the ability to delay the elimination of biomolecules from the circulation through a variety of mechanisms, including decreasing renal clearance, proteolysis and immunogenicity. PEGylation involves covalent attachment of PEG polymers to macromolecules, preferably to the primary amine of lysines.

This example describes the preparation of a PEGylated compstatin analog, Ac-V4(1-methyl-W)/H9A-K-PEG 5000 (SEQ ID NO:36) and evaluation of the compound for its ability to inhibit complement activation.

Fmoc-NH—NHS-5000 PEG was purchased from Nektar transforming therapeutics, 490 discovery Dr, Huntsville, Ala. 35806.

The compound Ac-V4(1-methyl-W)/H9A-K-PEG 5000 (SEQ ID NO:36) was synthesized chemically by Fmoc solid-phase peptide chemistry according to a modified standard protocol. Briefly, PEG was dissolved in 3 ml of dichloromethane, 1 ml of 2M DIEA was added manually, and the PEG was mixed for 5 minutes.

Then the PEG was transferred to the vessel, and left to couple overnight. The PEG was then deprotected with 20% piperidine for 20 min.

Then the synthesis proceeded according to the standard protocol, with a lysine incorporated at the C-terminus of the molecule for the purpose of linking the PEG to its side chain.

Final cleavages of the peptides was achieved with Reagent D (TFA:H2O:TIS:Phenol, 87.5:5:2.5:5) (4 mL) at 25C for 90 min, to provide the desired product. The peptide was then purified on a C18 reversed-phase HPLC column, lyophilized and characterized by MALDI-TOF.

Figure 7:
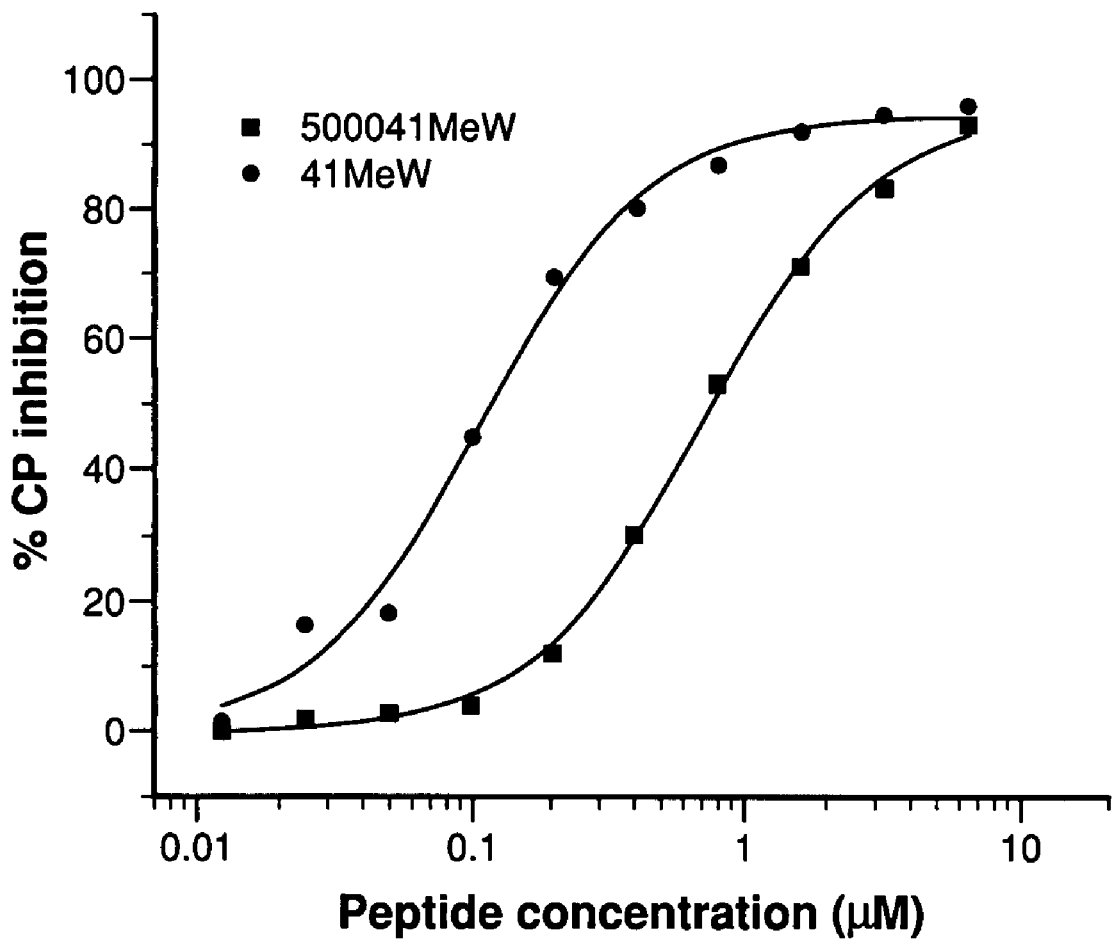
FIG. 7. Activity of the PEGylated compstatin analog. Plots of percent complement inhibition vs. peptide concentration for Ac-V4(1-methyl-W)/H9A (SEQ ID NO:23) (circles) and Ac-V4(1-methyl-W)/H9A-K-PEG 5000 (SEQ ID NO:36) (squares).

The PEGylated compstatin analog was tested for complement-inhibiting activity using the in vitro assay described in Example 4. As shown in FIG. 7, the PEGylated analog was active in inhibiting complement activation, however, seven-fold more conjugate was required to achieve the same amount of inhibition as the non-PEGylated analog, Ac-V4(1-methyl-W)/H9A (SEQ ID NO:23).

EXAMPLE 11

Albumin Binding Protein Conjugate of Compstatin Analog

Dennis et al. (2002) identified a series of peptides having the core sequence DICLPRWGCLW (SEQ ID NO:37) that specifically bound serum albumin from multiple species with high affinity. These peptides bound to albumin with 1:1 stoichiometry at a site distinct from known small molecule binding sites. The peptide SA21 (AcRLIEDICLPRWG-CLWEDDNH2; SEQ ID NO:38) has an unusually long half-life of 2.3 h when injected by intravenous bolus into rabbits. As mentioned in the Detailed Description, a related sequence, fused to the anti-tissue factor Fab of D3H44 enabled the Fab to bind albumin with similar affinity to that of SA21 while retaining the ability of the Fab to bind tissue factor1 (Nguyen et al. 2006). This interaction with albumin resulted in reduced in vivo clearance of 25- and 58-fold in mice and rabbits, respectively, when compared with the wild-type D3H44 Fab. The half-life was extended 37-fold to 32.4 h in rabbits and 26-fold to 10.4 h in mice, achieving 25-43% of the albumin half-life in these animals. These half-lives exceed those of a Fab 2 and are comparable with those seen for PEGylated Fab molecules, immunoadhesins, and albumin fusions.

This example describes the synthesis of a Compstatin analog fused with an albumin-binding peptide and its activity in in vitro assays for complement inhibition.

The compound 4(1MeW)-ABP was synthesized chemically by Fmoc solid-phase peptide chemistry according to standard protocols. The N- and C-termini of the peptide were protected with acetyl and amide groups. The peptide was further purified on a C18 reversed-phase HPLC column, lyophilized, and characterized by MALDI mass spectrometry.

For cyclization, the peptide-resin (0.10 mmol/g loading based on amino acid analysis) was swollen in dichloromethane (DCM) (2 mL) for 5 min, filtered and treated with 94:1:5 DCM/TFA/TIS (5 mL) at 25° C. 3 times×2 min each to selectively deprotect the S-Mmt protecting groups, removing the solvent N2 pressure. These bis(thiol), bis(Acm)-peptide-resin intermediates were washed with CH2Cl2, DMF and NMP (each 5 times×2 min, 2 mL), swollen further in NMP (2 mL) for 5 min and then treated with Et3N (2 eq.) in NMP at 25° C. for 4 h. The peptide-resin was then washed with DMF and CH2Cl2 (each 5 times×2 min, 2 mL). Following resin-bound formations of the first loop, the peptide-resin was again washed with DMF (5 times×2 min, 2 mL) and swollen in DMF (2 mL) for 5 min, filtered and treated with T1(tfa)3 (1.5 eq.) in DMF-anisole (4 mL) to cyclize the second disulfide loops. After gentle agitation at 25° C. for 4 h, the thallium reagents were removed with DMF (8 times×2 min, 2 mL) and the peptide-resins were washed further with CH2Cl2 (5 times×2 min, 2 mL). Final cleavages of the bicyclic peptide was achieved with Reagent D (TFA:H2O:TIS:Phenol, 87.5: 5:2.5:5) (4 mL) at 25° C. for 90 min, to provide the desired product.

The resultant conjugated peptide (SEQ ID NO:39) is shown below.

Figure 8:
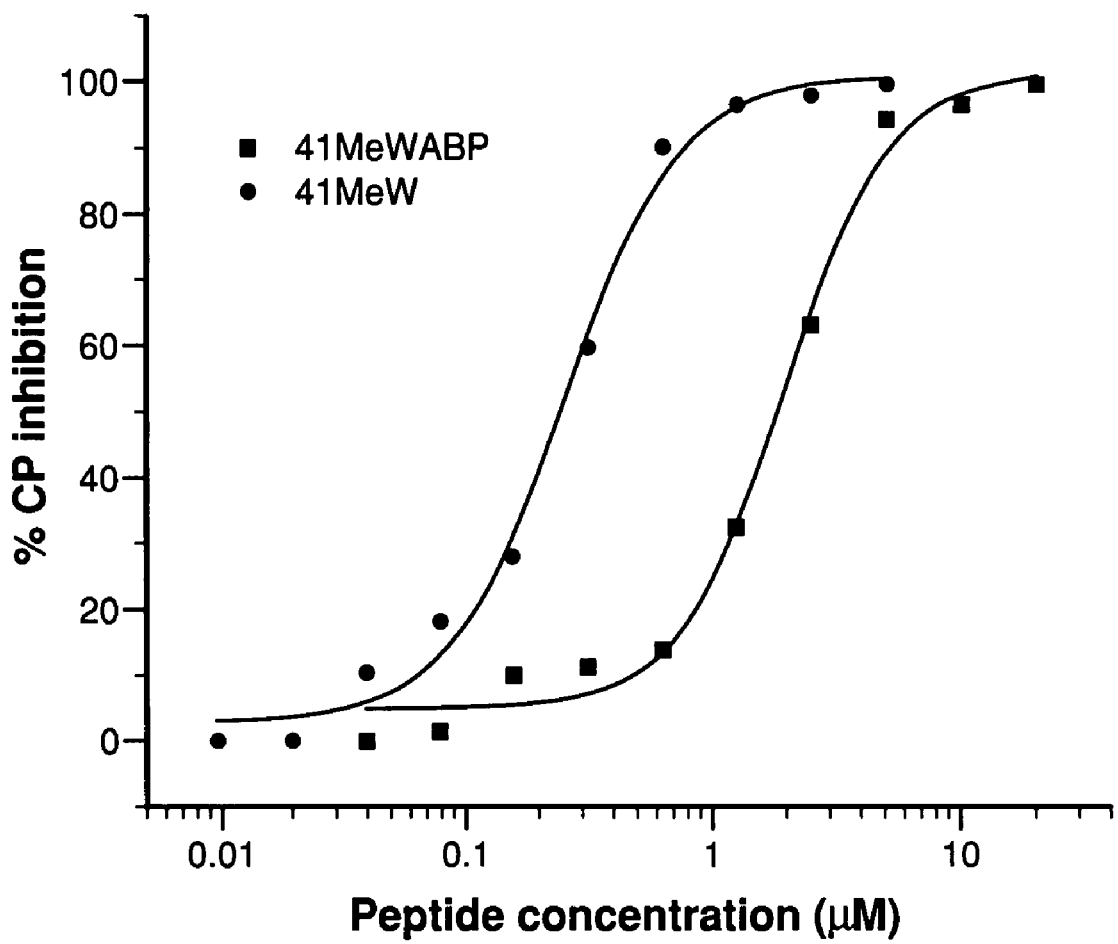
FIG. 8. Activity of the albumin binding protein-conjugated compstatin analog. Plots of percent complement inhibition vs. peptide concentration for Ac-V4(1-methyl-W)/H9A (SEQ ID NO:23) (circles) and the fusion peptide (Ac-ICV(1MeW)QDWGAHRCTRLIEDICLPRWGCLWEDD-NH$_2$) (SEQ ID NO:39) (squares).

The Albumin-binding peptide-compstatin was tested for complement-inhibiting activity using the in vitro assay described in Example 4. As shown in FIG. 8, the conjugate was active in inhibiting complement activation, however, seven-fold more conjugate was required to achieve the same amount of inhibition as the unconjugated analog, Ac-V4(1-methyl-W)/H9A (SEQ ID NO:23).

REFERENCES

Babitzke P, and Yanofsky C. (1995) Structural features of L-tryptophan required for activation of TRAP, the trp RNA-binding attenuation protein of *Bacillus subtilis. J. Biol. Chem.* 270:12452-6.

Beeley N. (1994) Peptidomimetics and small-molecule drug design: towards improved bioavailability and in vivo stability. *Trends Biotechnol.* 12:213-6.

Beene D L, Brandt G S, Zhong W, Zacharias N M, Lester H A, and Dougherty D A. (2002) Cation-pi interactions in ligand recognition by serotonergic (5-HT3A) and nicotinic acetylcholine receptors: the anomalous binding properties of nicotine. *Biochemistry.* 41:10262-9.

Dennis M S, Zhang M, Meng Y G, Kadkhodayan M, Kirchhofer D, Combs D, Damico L A. (2002) Albumin binding as a general strategy for improving the pharmacokinetics of proteins. *J Biol. Chem.* 277:35035-43

Fiane A E, Mollnes T E, Videm V, Hovig T, Hogasen K, Mellbye O J, Spruce L, Moore W T, Sahu A, and Lambris J D. (1999a) Prolongation of ex vivo-perfused pig xenograft survival by the complement inhibitor Compstatin. *Transplant. Proc.* 31:934-5.

Fiane A E, Mollnes T E, Videm V, Hovig T, Hogasen K, Mellbye O J, Spruce L, Moore W T, Sahu A, and Lambris J D. (1999b) Compstatin, a peptide inhibitor of C3, prolongs survival of ex vivo perfused pig xenografts. *Xenotransplantation.* 6:52-65.

Fiane A E, Videm V, Lambris J D, Geiran O R, Svennevig J L, and Mollnes T E. (2000) Modulation of fluid-phase complement activation inhibits hyperacute rejection in a porcine-to-human xenograft model. *Transplant. Proc.* 32:899-900.

Furlong S T, Dutta A S, Coath M M, Gormley J J, Hubbs S J, Lloyd D, Mauger R C, Strimpler A M, Sylvester M A, Scott C W, and Edwards P D. (2000) C3 activation is inhibited by analogs of compstatin but not by serine protease inhibitors or peptidyl alpha-ketoheterocycles. *Immunopharmacology.* 48:199-212.

Hruby V J. (1993) Conformational and topographical considerations in the design of biologically active peptides. *Biopolymers.* 33:1073-82.

Kalli K R, Hsu P, Fearon and D T. (1994) Therapeutic uses of recombinant complement protein inhibitors. *Springer Semin. Immunopathol.* 15:417-31.

Katragadda M, Morikis D, and Lambris J D. (2004) Thermodynamic studies on the interaction of the third complement component and its inhibitor, compstatin. *J. Biol. Chem.* 279:54987-95.

Klepeis J L, Floudas C A, Morikis D, Tsokos C G, Argyropoulos E, Spruce L, and Lambris J D. (2003) Integrated computational and experimental approach for lead optimization and design of compstatin variants with improved activity. *J. Am. Chem. Soc.* 125:8422-3.

Kozlowski A, Charles S A, and Harris J M. (2001) Development of pegylated interferons for the treatment of chronic hepatitis C. *BioDrugs.* 15:419-29.

Mallik B, Katragadda M, Spruce L A, Carafides C, Tsokos C G, Morikis D, and Lambris J D (2005) Design and NMR Characterization of Active Analogs of Compstatin Containing Non-Natural Amino Acids. *J. Med. Chem.* 48:274-286.

Morikis D, Assa-Munt N, Sahu A, and Lambris J D. (1998) Solution structure of Compstatin, a potent complement inhibitor. *Protein Sci.* 7:619-27.

Nguyen A, Reyes A E 2nd, Zhang M, McDonald P, Wong W L, Damico L A, Dennis M S. (2006) The pharmacokinetics of an albumin-binding Fab (AB.Fab) can be modulated as a function of affinity for albumin. *Protein Eng Des Sel.* 19:291-7.

Nilsson B, Larsson R, Hong J, Elgue G, Ekdahl K N, Sahu A, and Lambris J D. (1998) Compstatin inhibits complement and cellular activation in whole blood in two models of extracorporeal circulation. *Blood.* 92:1661-7.

Sahu A, Kay B K, and Lambris J D. (1996) Inhibition of human complement by a C3-binding peptide isolated from a phage-displayed random peptide library. *J. Immunol.* 157:884-91.

Soulika A M, Khan M M, Hattori T, Bowen F W, Richardson B A, Hack C E, Sahu A, Edmunds L H Jr, and Lambris J D. (2000) Inhibition of heparin/protamine complex-induced complement activation by Compstatin in baboons. *Clin. Immunol.* 96:212-21.

Spruce L., E. Argyropoulos, D. Mastellos, G. Sfyroera, and J. D. Lambris (2002) Chemical synthesis of small complement proteins and protein modules. *International Immunopharmacology.* 2: 1320-1321.

Veronese F M. (2001) Peptide and protein PEGylation: a review of problems and solutions. *Biomaterials* 22:405-417.

Wang Y, Hu Q, Madri J A, Rollins S A, Chodera A, and Matis L A. (1996) Amelioration of lupus-like autoimmune disease in NZB/WF1 mice after treatment with a blocking monoclonal antibody specific for complement component C5. *Proc. Natl. Acad. Sci. USA.* 93:8563-8.

Zhao B, Helms L R, DesJarlais R L, Abdel-Meguid S S, and Wetzel R. (1995) A paradigm for drug discovery using a conformation from the crystal structure of a presentation scaffold. *Nat. Struct. Biol.* 2:1131-7.

The present invention is not limited to the embodiments described and exemplified above, but is capable of variation and modification within the scope of the appended claims.

What is claimed:

1. A compound that inhibits complement activation, comprising a peptide having a sequence:

(SEQ ID NO: 26)
Xaa1-Cys-Val-Xaa2-Gln-Asp-Xaa3-Gly-Xaa4-His-Arg-Cys-Xaa5;

wherein:
Xaa1 is Ile, Val, Leu, Ac-Ile, Ac-Val, Ac-Leu or a dipeptide comprising Gly-Ile;
Xaa2 is Trp or an analog of Trp, wherein the analog of Trp has increased hydrophobic character as compared with Trp, with the proviso that, if Xaa3 is Trp, Xaa2 is the analog of Trp comprising 5-fluoro-l-tryptophan, or 6-fluoro-l-tryptophan, or 5-methoxytryptophan, or 5-methyltryptophan, or 1-methyltryptophan, or 1-formyltryptophan;
Xaa3 is Trp or an analog of Trp comprising a chemical modification to its indole ring wherein the chemical modification increases the hydrogen bond potential of the indole ring;
Xaa4 is His, Ala, Phe or Trp;
Xaa5 is L-Thr, D-Thr, Ile, Val, Gly, a dipeptide comprising Thr-Asn or Thr-Ala, or a tripeptide comprising Thr-Ala-Asn, wherein a carboxy terminal —OH of any of the L-Thr, D-Thr, Ile, Val, Gly or Asn optionally is replaced by —NH2; and
the two Cys residues are joined by a disulfide bond.

2. The compound of claim 1, wherein Xaa3 is an analog of Trp and Xaa2 is an analog of Trp that participates in a nonpolar interaction with C3.

3. The compound of claim 2, wherein Xaa3 is an analog of Trp and that participates in a hydrogen bond with C3, and Xaa2 is an analog of Trp that participates in a nonpolar interaction with C3.

4. The compound of claim 1, wherein Xaa3 is an analog of Trp that participates in a hydrogen bond with C3.

5. The compound of claim 1, wherein Xaa3 is an analog of Trp, and Xaa2 is an analog of Trp comprising halogenated tryptophan.

6. The compound of claim 5, wherein the halogenated tryptophan is 5-fluoro-1-tryptophan, or 6-fluoro-1-tryptophan.

7. The compound of claim 1, wherein Xaa3 is an analog of Trp, and Xaa2 is an analog of Trp comprising a lower alkoxy or lower alkyl substituent at the 1 or 5 position of tryptophan.

8. The compound of claim 7, wherein the analog of Trp of Xaa2 is 5-methoxytryptophan or 5-methyltryptophan or 1-methyltryptophan or 1-formyltryptophan.

9. The compound of claim 1, wherein Xaa3 is an analog of Trp, and Xaa2 is an analog of Trp comprising a lower alkanoyl or lower alkyl substituent at the 1 position of tryptophan.

10. The compound of claim 9, wherein the analog of Trp of Xaa2 is 1-methyltryptophan or 1-formyltryptophan.

11. The compound of claim 1, wherein the analog of Trp of Xaa3 comprises a halogenated tryptophan.

12. The compound of claim 11, wherein the halogenated tryptophan is 5-fluoro-1-tryptophan, or 6-fluoro-1-tryptophan.

13. The compound of claim 1, wherein Xaa4 is Ala.

14. The compound of claim 1, wherein Xaa2 comprises a lower alkanoyl or lower alkyl substituent at the 1 position of tryptophan, Xaa3 optionally comprises a halogenated tryptophan and Xaa4 comprises Alanine, with the proviso that, if Xaa3 is Trp instead of halogenated tryptophan, Xaa2 is an analog of Trp comprising 1-methyltryptophan, or 1-formyltryptophan.

15. The compound of claim 14, wherein Xaa2 is 1-methyltryptophan or 1-formyltryptophan and Xaa3 optionally comprises 5-fluoro-1-tryptophan.

16. The compound of claim 1, comprising any of SEQ ID NOS: 16 -25.

17. The compound of claim 1, which comprises a peptide produced by expression of a polynucleotide encoding the peptide.

18. The compound of claim 1, wherein the compound is produced at least in part by peptide synthesis.

19. The compound of claim 16, comprising any one of SEQ ID NOS: 23, 24 or 25.

20. The compound of claim 1, wherein the compound is PEGylated.

21. The compound of claim 20, comprising SEQ ID NO:36.

22. The compound of claim 1, further comprising an additional peptide component that extends the in vivo retention of the compound.

23. The compound of claim 22, wherein the additional peptide component is an albumin binding peptide.

24. The compound of claim 23, comprising SEQ ID NO:39.

25. The compound of claim 1, which binds C3 and inhibits complement activation with at least 100-fold greater activity than does a peptide comprising SEQ ID NO:1 under equivalent assay conditions.

* * * * *